(12) United States Patent
Salam et al.

(10) Patent No.: US 10,894,757 B2
(45) Date of Patent: *Jan. 19, 2021

(54) PT/SRTIO$_3$ PHOTOCATALYST FOR PRODUCTION OF CYCLOALKANOLS AND CYCLOALKANONES FROM CYCLOALKANES

(71) Applicant: King Abdulaziz University, Jeddah (SA)

(72) Inventors: Mohamed Abdel Salam, Jeddah (SA); Hind Al-Johani, Jeddah (SA)

(73) Assignee: King Abdulaziz University, Jeddah (SA)

( * ) Notice: Subject to any disclaimer, the term of this patent is extended or adjusted under 35 U.S.C. 154(b) by 580 days.

This patent is subject to a terminal disclaimer.

(21) Appl. No.: 15/916,370

(22) Filed: Mar. 9, 2018

(65) Prior Publication Data

US 2019/0276383 A1    Sep. 12, 2019

(51) Int. Cl.
*B01J 37/34* (2006.01)
*C07C 29/48* (2006.01)
(Continued)

(52) U.S. Cl.
CPC ............. *C07C 29/48* (2013.01); *B01J 21/063* (2013.01); *B01J 23/58* (2013.01); *B01J 23/92* (2013.01);
(Continued)

(58) Field of Classification Search
CPC ......... C07C 29/48; C07C 45/27; C07C 35/08; C07C 49/11; C07C 45/33; C07C 2601/14; C07C 29/50; B01J 21/063; B01J 23/58; B01J 23/92; B01J 35/004; B01J 35/023; B01J 35/1014; B01J 37/0219; B01J 37/0236; B01J 37/04; B01J 37/08; B01J 37/16; B01J 37/345; B01J 2523/828; B01J 2523/24; B01J 2523/47; B01J 37/343; B01J 37/033; B01J 35/002
See application file for complete search history.

(56) References Cited

U.S. PATENT DOCUMENTS 4,861,484 A * 8/1989 Lichtin ................. B01J 21/063
                                              210/638
6,124,505 A * 9/2000 Haruta ..................... B01J 23/52
                                              502/243
(Continued)

OTHER PUBLICATIONS

J. S. Jang and J. S. Lee, Platinum Nanoparticle Co-Catalyst-Induced Improved Photoelectrical Properties in a Chromium-Doped SrTiO3 Photocatalyst, Dec. 2009, vol. 55/6, p. 2470-2475, http://www.ikps.or.kr/journal/download_pdf.

(Continued)

*Primary Examiner* — Haytham Soliman
(74) *Attorney, Agent, or Firm* — Oblon, McClelland, Maier & Neustadt, L.L.P.

(57) ABSTRACT

Methods of preparing Pt/SrTiO$_3$ photocatalysts comprising strontium titanate nanoparticles and platinum doped on a surface of the strontium titanate nanoparticles are described. Processes of oxidizing cycloalkanes to cycloalkanols and/or cycloalkanones by employing the Pt/SrTiO$_3$ photocatalysts are specified. A method for recycling the photocatalyst is also provided.

18 Claims, 7 Drawing Sheets

(51) Int. Cl.
  B01J 21/06    (2006.01)
  B01J 23/58    (2006.01)
  B01J 23/92    (2006.01)
  B01J 35/00    (2006.01)
  B01J 35/02    (2006.01)
  B01J 35/10    (2006.01)
  B01J 37/02    (2006.01)
  B01J 37/04    (2006.01)
  B01J 37/08    (2006.01)
  B01J 37/16    (2006.01)
  C07C 45/27    (2006.01)
  C07C 35/08    (2006.01)
  C07C 49/11    (2006.01)

(52) U.S. Cl.
  CPC ........... *B01J 35/004* (2013.01); *B01J 35/023* (2013.01); *B01J 35/1014* (2013.01); *B01J 37/0219* (2013.01); *B01J 37/0236* (2013.01); *B01J 37/04* (2013.01); *B01J 37/08* (2013.01); *B01J 37/16* (2013.01); *B01J 37/345* (2013.01); *C07C 45/27* (2013.01); *B01J 2523/24* (2013.01); *B01J 2523/47* (2013.01); *B01J 2523/828* (2013.01); *C07C 35/08* (2013.01); *C07C 49/11* (2013.01)

(56) References Cited

U.S. PATENT DOCUMENTS

2015/0107984 A1    4/2015    Tokudome et al.
2015/0251172 A1*   9/2015    Tokudome ............ B01J 21/063
                                                      428/323
2017/0232423 A1    8/2017    Bai et al.

OTHER PUBLICATIONS

Duo-Nguyen Bui, Jin Mu, Lei Wang, Shi-Zhao Kang, Xiangqing Li, Preparation of Cu-loaded SrTiO3 nanoparticles and their photocatalytic activity for hydrogen evolution from methanol aqueous solution, Jun. 1, 2013, vol. 274, p. 328-333, http://www.sciencedirect.com/science/pii/S0169433213005229.

J. Wang, J. Zhao and F. E. Osterloh, Photochemical charge transfer observed in nanoscale hydrogen evolving photocatalysts using surface photovoltage spectroscopy, Jul. 13, 2015, vol. 08, p. 2970-2976, http://pubs.rsc.org/en/content/articlelanding/2015/ee/c5ee01701g#!divAbstract.

Tarawipa Puangpetch, Thammanoon Sreethawong, Susumu Yoshikawa, Sumaeth Chavadej, Hydrogen production from photocatalytic water splitting over mesoporous-assembled SrTiO3 nanocrystal-based photocatalysts, Oct. 1, 2009, vol. 312/1-2, p. 97-106, http://www.sciencedirect.com/science/article/pii/S1381116909003434.

Ana Rita Almeida, Jacob A. Moulijn, and Guido Mul, Photocatalytic Oxidation of Cyclohexane over TiO2: Evidence for a Mars-van Krevelen Mechanism, Jan. 5, 2011, vol. 115/4, p. 1330-1338, http://pubs.acs.org/doi/abs/10.1021/ip107290r.

James A. Enterkin, Worajit Setthapun, Jeffrey W. Elam, Steven T. Christensen, Federico A. Rabuffetti, Laurence D. Marks, Peter C. Stair, Kenneth R. Poeppeimeier, and Christopher L. Marshall, Propane Oxidation over Pt/SrTiO3 Nanocuboids, Apr. 28, 2011, vol. 1/6, p. 629-635, http://pubs.acs.org/doi/abs/10.1021/cs200092c.

* cited by examiner

PT/SRTIO₃ PHOTOCATALYST FOR PRODUCTION OF CYCLOALKANOLS AND CYCLOALKANONES FROM CYCLOALKANES

STATEMENT REGARDING PRIOR DISCLOSURE BY THE INVENTORS

Aspects of this technology are described in an article "Enhancement of visible light irradiation photocatalytic activity of SrTiO₃ nanoparticles by Pt doping for oxidation of cyclohexane" published in Journal of Chemical Sciences, 2017, 129, 1687-1693, on Sep. 25, 2017, which is incorporated herein by reference in its entirety.

BACKGROUND OF THE INVENTION

Technical Field

The present invention relates to a method of synthesizing a Pt/SrTiO₃ photocatalyst comprising strontium titanate nanoparticles and platinum doped on a surface of the photocatalyst and a process of producing cycloalkanols and/or cycloalkanones by oxidizing cycloalkanes utilizing the Pt/SrTiO₃ photocatalyst.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of tiling, are neither expressly or impliedly admitted as prior art against the present invention.

As major components in oil and national gas, alkanes serve as synthetic precursors to many chemicals. For example, selective oxidation of cyclohexane is a major process for producing KA-oil, which consists of a mixture of cyclohexanol and cyclohexanone [Urus S. Adigüzel H and Incesu M 2016. Synthesis of novel $N_4O_4$ type bis(diazoimine)-metal complexes supported on mesoporous silica: Microwave assisted catalytic oxidation of cyclohexane, cyclooctane, cyclohexene and styrene Chem. Eng. J. 296, 90; and Loncarevic D, Krstic J, Dostanic J, Manojlovic D, Cupic Z and Jovanovic D M 2010. Cyclohexane oxidation and cyclohexyl hydroperoxide decomposition by poly(4-vinylpyridine-co-divinylbenzene) supported cobalt and chromium complexes Chem. Eng. J. 157, 181], KA-oil is an important intermediate in the petrochemical industry for production of various polymers such as nylon [Silva A R, Mourão T and Rocha J 2013. Oxidation of cyclohexane by transition-metal complexes with biomimetic ligands Catal. Today 203, 81]. Therefore, selective oxidation of cyclohexane is of great importance for scientific and industrial applications. Currently, selective oxidation of cyclohexane is costly because it is an energy-consuming process that requires high temperature and pressure. In addition, undesired by-products such as toluene, methyl-cyclohexane, heptene, 1-hexene, and 5-hexanal are often generated during the oxidation process, which lower production yield and complicate recovery/separation steps [Liu S, Liu Z and Kawi S 1998 Liquid-phase oxidation of cyclohexane using Co-P-MCM-41 catalyst Korean J. Chem. Eng. 15, 510]. Scientific communities all around the globe are focused on developing highly selective and efficient methods for selective oxidation of cyclohexane. A possible alternative process is photocatalytic oxidation, which is widely applied in different fields e.g. chemical production [Chen J, Cen J, Xu X and Li X 2016. The application of heterogeneous visible light photocatalysts in organic synthesis Catal. Sci. Technol. 6, 349]; water remediation [Lee S-Y and Park S-J 2013 $TiO_2$ photocatalyst for water treatment applications J. Ind. Eng. Chem. 19, 1761], and air purification [Luengas A, Barona A, Hort C, Gallastegui G, Platel V and Elias A 2015. A review of indoor air treatment technologies Rev. Environ. Sci. Biotechnol. 14, 499]. Due to their unique characteristics, transition metal oxides and semiconductors are commonly used as heterogeneous photocatalysts [Litter M I 1999 Heterogeneous photocatalysis: Transition metal ions in photocatalytic systems Appl. Catal. B 23, 89]. However, there is a limited amount of research devoted to developing photocatalysts for organic synthesis such as selective oxidation of alkanes [Carneiro J T, Yang C-C, Moulijn J A and Mul G 2011. The effect of water on the performance of $TiO_2$ in photocatalytic selective alkane oxidation J. Catal. 277, 129; Zhong W, Qiao T, Dai J. Mao L, Xu Q, Zou G, Liu X, Yin D and Zhao F 2015. Visible-light-responsive sulfated vanadium-doped TS-1 with hollow structure: enhanced photocatalytic activity in selective oxidation of cyclohexane J. Catal. 330, 208; and Kim J, Ichikuni N, Hara T and Shimazu S 2016. Study on the selectivity of propane photo-oxidation reaction on SBA-15 supported Mo oxide catalyst Catal. Today 265, 90, each incorporated herein by reference in their entirety].

SrTiO₃ is an oxide semiconductor and a potential photocatalyst [Yu K, Zhang C, Chang Y, Feng Y, Yang Z, Yang T, Lou L-L and Liu S 2017. Novel three-dimensionally ordered macroporous SrTiO₃ photocatalysts with remarkably enhanced hydrogen production performance Appl. Catal. B 200; 514; He G-L, Zhong Y-H, Chen M-J, Li X, Fang Y-P and Xu Y-H 2016. One-pot hydrothermal synthesis of SrTiO₃-reduced graphene oxide composites with enhanced photocatalytic activity for hydrogen production J. Mol. Catal. A 423, 70; Xu Y and Schoonen M A A 2000. The absolute energy positions of conduction and valence bands of selected semiconducting minerals Am. Mineral. 85, 543; Yu H, Ouyang S, Yan S, Li Z, Yu T and Zou Z 2011. Sol-gel hydrothermal synthesis of visible-light-driven Cr-doped SrTiO₃ for efficient hydrogen production J. Mater. Chem. 21, 11347; and Wang D, Ye J, Kako T and Kimura T 2006. Photophysical and photocatalytic properties of SrTiO₃ doped with Cr cations on different sites J. Phys. Chem. B 110, 15824, each incorporated herein by reference in their entirety]. It is possible to enhance the photocatalytic activity of SrTiO₃ in the visible light region by doping it with other metal or metal oxides. For instance, doping SrTiO₃ with Rh enhanced the catalytic properties of SrTiO₃ photocatalyst for hydrogen production [Shen P, Lofaro Jr. J C, Woerner W R, White M G, Su D and Orlov A 2013. Photocatalytic activity of hydrogen evolution over Rh doped SrTiO₃ prepared by polymerizable complex method Chem. Eng. J. 223, 200, incorporated herein by reference in its entirety], doping SrTiO₃ with Cr enhanced its photocatalytic activity for the visible-light driven transformation of $CO_2$ to $CH_4$ [Bi Y, Ehsan M F, Huang Y, Jin J and He T 2015 Synthesis of Cr-doped SrTiO₃ photocatalyst and its application in visible-light-driven transformation of $CO_2$ into $CH_4$ J. $CO_2$ Util. 12, 43, incorporated herein by reference in its entirety], and macroporous monolithic photocatalyst prepared by doping SrTiO₃ with $TiO_2$ and nitrogen was used for photodegradation of Rhodamine B organic dye under visible light [Ruzimuradov O, Sharipov K, Yarbekov A, Saidov K, Hojamberdiev M, Prasad R M, Cherkashinin G and Riedel R 2015.

A facile preparation of dual-phase nitrogen-doped $TiO_2SrTiO_3$ macroporous monolithic photocatalyst for organic dye photodegradation under visible light J. Eur. Ceram. Soc, 35, 1815, incorporated herein by reference in its entirety]. It was also reported that construction of a heterojunction by doping $SrTiO_3$ with $Bi_2O_3$ facilitated degradation of tetracycline under visible light [Che H, Chen Jr, Huang K, Hu W, Hu H, Liu X, Che G, Liu C and Shi W 2016. Construction of $SrTiO_3/Bi_2O_3$ heterojunction towards to improved separation efficiency of charge carriers and photocatalytic activity under visible light J. Alloys Compd. 688, 882, incorporated herein by reference in its entirety], and utilization of $BiVO_4/SrTiO_3$ composite for photocatalytic degradation of the antibiotic sulfamethoxazole under sunlight [Li Jr, Wang F, Meng L, Han M, Guo Y and Sun C 2017. Controlled synthesis of $BiVO_4/SrTiO_3$ composite with enhanced sunlight-driven photofunctions for sulfamethoxazole removal J. Colloid Interface Sci. 485, 116, incorporated herein by reference in its entirety]. Further, doping $AgInS_2$ nanoparticles with Pt enhanced the photocatalytic oxidation of cyanide in water under visible light [Azam E S 2014. Photocatalytic oxidation of cyanide under visible light by Pt doped $AgInS_2$ nanoparticles J. Ind. Eng. Chem. 20, 4008, incorporated herein by reference in its entirety], while Pt doped $TiO_2$ nanoparticles [Xiong Z, Wang H, Xu N, Li H, Fang B, Zhao Y, Zhang J and Zheng C 2015. Photocatalytic reduction of $CO_2$, on $Pt^{24}$—$Pt^0/TiO_2$ nanoparticles under UV/V is light irradiation: A combination of $Pt^{24}$ doping and Pt nanoparticles deposition J. Hydrogen Energy 40, 10049, incorporated herein by reference in its entirety] and graphitic carbon nitride (g-$C_3N_4$) [Ong W-J, Tan L-L, Chai S-P and Yong S-T 2015. Heterojunction engineering of graphitic carbon nitride (g-$C_3N_4$) via Pt loading with improved daylight-induced photocatalytic reduction of carbon dioxide to methane Dalton Trans. 44, 1249, incorporated herein by reference in its entirety] were used for photocatalytic reduction of $CO_2$ to $CH_4$. However, these existing photocatalysts often suffer from various problems including low efficiency, unsatisfactory stability and positive impact on charge recombination, which jeopardize their catalytic performance.

In view of the forgoing, one objective of the present invention is to provide a process of oxidizing cycloalkanes to cycloalkanols and/or cycloalkanones in the presence of a $Pt/SrTiO_3$ photocatalyst and an oxidant. Another objective of the present disclosure is to provide a method of preparing the $Pt/SrTiO_3$ photocatalyst.

BRIEF SUMMARY OF THE INVENTION

According to a first aspect, the present disclosure relates to a process of oxidizing a cycloalkane to a cycloalkanol and/or a cycloalkanone. The process involves contacting a feed mixture comprising the cycloalkane and an oxidant with a $Pt/SrTiO_3$ photocatalyst thereby forming a reaction mixture, and concurrently irradiating the reaction mixture with light thereby forming the cycloalkanol and/or the cycloalkanone, wherein the $Pt/SrTiO_3$ photocatalyst includes (i) strontium titanate nanoparticles, and (ii) platinum doped on a surface of the strontium titanate nanoparticles, in which the platinum is present in an amount of 0.1-5.0 wt % relative to a total weight of the $Pt/SrTiO_3$ photocatalyst.

In one embodiment, the $Pt/SrTiO_3$ photocatalyst has a crystallite size of 8-30 nm.

In one embodiment, the $Pt/SrTiO_3$ photocatalyst has a BET surface area of 5-25 $m^2/g$.

In one embodiment, the $Pt/SrTiO_3$ photocatalyst has an absorption peak in a range of 360-380 nm, and a band gap energy of 2.5-3.6 eV.

In one embodiment, the $Pt/SrTiO_3$ photocatalyst has a photoluminescence peak in a range of 380-480 nm upon excitation at a wavelength of 270-290 nm.

In one embodiment, the light has a wavelength of 400-800 nm.

In one embodiment, the feed mixture is contacted with the $Pt/SrTiO_3$ photocatalyst at a pressure of 0.5-2 atm.

In one embodiment, the feed mixture is contacted with the $Pt/SrTiO_3$ photocatalyst at a temperature of 40-80° C.

In one embodiment, the cycloalkane is present in the feed mixture at a concentration of 10-400 ppm.

In one embodiment, the oxidant is present in an amount of 5-30 vol. %) relative to a total volume of the feed mixture.

In one embodiment, the $Pt/SrTiO_3$ photocatalyst is present at a concentration of 0.2-5.0 g of photocatalyst per liter of the reaction mixture.

In one embodiment, the oxidant is $O_2$.

In one embodiment, the feed mixture further comprises an inert gas.

In one embodiment, the feed mixture further comprises water.

In one embodiment, the process has a molar conversion of the cycloalkane to the cycloalkanol and/or the cycloalkanone of greater than 40%.

In one embodiment, the cycloalkane is cyclohexane, the cycloalkanol is cyclohexanol, and the cycloalkanone is cyclohexanone.

In one embodiment, the platinum is present in an amount of 1.3-3.0 wt % relative to a total weight of the $Pt/SrTiO_3$ photocatalyst, the reaction mixture is irradiated with light for 1 to 4 hours, and the process has a molar conversion of the cycloalkane to the cycloalkanol and/or the cycloalkanone of greater than 95%.

In one embodiment, the process further comprises (i) recovering the $Pi/SrTiO_3$ photocatalyst after the irradiating to obtain a recovered $Pt/SrTiO_3$ photocatalyst, and (ii) reusing the recovered $Pt/SrTiO_3$ photocatalyst, which maintains photocatalytic activity for at least 4 reaction cycles.

According to a second aspect, the present disclosure relates to a method of producing a $Pt/SrTiO_3$ photocatalyst comprising strontium titanate nanoparticles and platinum doped on a surface of the strontium titanate nanoparticles. The method includes (i) mixing a strontium(II) salt with an acid to form a first mixture, (ii) adding a titanium(IV) alkoxide to the first mixture to form a second mixture, (iii) sonicating, drying and calcining the second mixture to form strontium titanate nanoparticles, (iv) mixing a platinum(II) compound with the strontium titanate nanoparticles to form a third mixture, and (v) reducing the third mixture with a reductant to form the $Pt/SrTiO_3$ photocatalyst.

In one embodiment, the platinum(II) compound is mixed with the strontium titanate nanoparticles under ultraviolet radiation.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
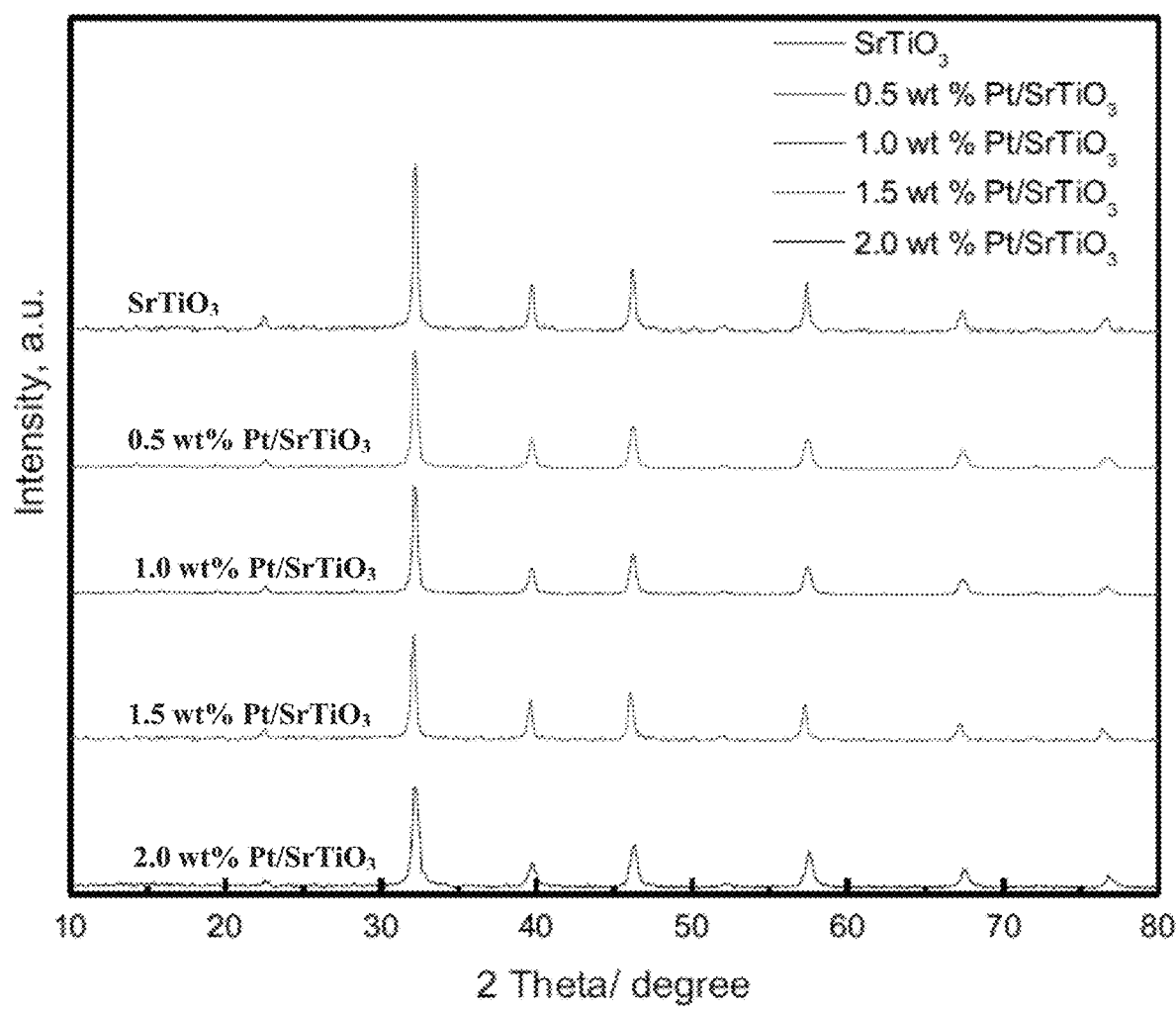
FIG. 1 is an overlay of the X-ray diffraction (XRD) patterns of strontium titanate nanoparticles ($SrTiO_3$), and $Pt/SrTiO_3$ photocatalysts containing 0.5 wt % (0.5 wt % $Pt/SrTiO_3$), 1.0 wt % (1.0 wt % $Pt/SrTiO_3$), 1.5 wt % (1.5 wt % $Pt/SrTiO_3$), and 2.0 wt % (2.0 wt % $Pt/SrTiO_3$) of platinum relative to a total weight of each $Pt/SrTiO_3$ photocatalyst.

Embodiments of the present disclosure will now be described more fully hereinafter with reference to the accompanying drawings, in which some, but not all embodiments of the disclosure are shown.

The present disclosure will be better understood with reference to the following terms and meanings set forth below. Unless defined otherwise, all technical and scientific terms used herein have the same meaning as commonly understood to one of ordinary skill in the art.

As used herein, the words "a" and "an" and the like carry the meaning of "one or more." Within the description of this disclosure, where a numerical limit or range is stated, the endpoints are included unless stated otherwise. Also, all values and subranges within a numerical limit or range are specifically included as if explicitly written out.

As used herein, the term "compound" refers to a chemical entity, whether in a solid, liquid or gaseous phase, and whether in a crude mixture or purified and isolated.

Exemplary solvents useful for the present disclosure include, but are not limited to, organic solvents, e.g. alcohols such as methanol, ethanol, trifluoroethanol, n-propanol, i-propanol, n-butanol, i-butanol, i-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, and cyclohexanol, amide solvents such as dimethylformamide (DMF), dimethylacetamide (DMA), and N-methyl-2-pyrrolidone (NMP), aromatic solvents such as benzene, o-xylene, m-xylene, p-xylene, and mixtures of xylenes, toluene, mesitylene, anisole, 1,2-dimethoxybenzene, $\alpha,\alpha,\alpha$,-trifluoromethylbenzene, and fluorobenzene, chlorinated solvents such as chlorobenzene, dichloromethane (DCM), 1,2-dichloroethane, 1,1-dichloroethane, and chloroform, ester solvents such as ethyl acetate, and propyl acetate, ethers such as diethyl ether, tetrahydrofuran (THF), 1,4-dioxane, tetrahydropyran, tert-butyl methyl ether, cyclopentyl methyl ether, and di-isopropyl ether, glycol ethers such as 1,2-dimethoxyethane, diglyme, and triglyme, acetone, acetonitrile, propionitrile, butyronitrile, benzonitrile, dimethyl sulfoxide (DMSO), water, e.g. tap water, distilled water, doubly distilled water, deionized water, and deionized distilled water, and mixtures thereof in suitable proportions.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from the exemplary group including, but not limited to, halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanylamino, aroylamino, aralkanoylamino, substituted alkanoylamino, substituted arylamino, substituted aralkanoylamino, thiol, alkylthio, arylthio, arylalkythio, alkylthiono, arylthiono, aryalkylthiono, alkylsulfonyl, arylsulfonyl; arylalkylsulfonyl, sulfonamide (e.g. —$SO_2NH_2$), substituted sulfonamide, nitro, cyano, carboxy, carbamyl (e.g. —$CONH_2$), substituted carbamyl (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, fury, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like.

As used herein, the term "alkyl" unless otherwise specified refers to both branched and straight chain saturated aliphatic primary, secondary, and/or tertiary hydrocarbons of typically $C_1$ to $C_{12}$, preferably $C_2$ to $C_8$, and specifically includes, but is not limited to, methyl, trifluoromethyl, ethyl, n-propyl, isopropyl, n-butyl, sec-butyl, isobutyl, t-butyl, pentyl, isopentyl, neopentyl, hexyl, isohexyl, 3-methylpentyl, 2,2-dimethylbutyl, and 2,3-dimethylbutyl.

As used herein, the term "cycloalkane" refers to an optionally substituted alicyclic hydrocarbon of typically $C_3$ to $C_{30}$, preferably $C_4$-$C_{20}$, more preferably $C_5$-$C_{16}$, and specifically includes, but is not limited to, cyclopropane, cyclobutane, cyclopentane, cyclohexane, cycloheptane, cyclooctane, cyclononane, cyclodecane, cyclododecane, cyclotetradecane, cyclohexadecane, cyclooctadecane, cycloicosane, cyclodocosane, cyclotriacontane, decalin, adamantane, methylcyclopentane, methylcyclohexane, 1,1-dimethylcyclohexane, 1,2-dimethylcyclohexane, and 1,3-dimethylcyclohexane.

As used herein, the term "cycloalkanol" refers to a cycloalkane having at least one hydroxyl functional group (—OH) on an alicyclic ring. Exemplary cycloalkanols include, without limitation, cyclobutanol, cyclopentanol, cyclohexanol, cycloheptanol, cyclooctanol, cyclononanol, cyclodecanol, cycloundecanol, cyclododecanol, cyclopentadecanol, decahydro-2-naphthol, 1-methylcyclohexanol, 2-methylcyclohexanol, 4-methylcyclohexanol, 1-ethylcyclopentanol, 1,2-dimethylcyclohexanol, 2,2-dimethylcyclohexanol, 3,4-dimethylcyclohexanol, 3,3,5-trimethylcyclohexanol, and 1-methylcyclohexane-1,2-diol.

As used herein, the term "cycloalkanone" refers to a cycloalkane having at least one ketone functional group (>C=O) on an alicyclic ring. Exemplary cycloalkanones include, without limitation, cyclobutanone, cyclopentanone, cyclohexanone, cycloheptanone, cyclooctanone, cyclononanone, cyclodecanone, cycloundecanone, cyclododecanone, cyclopentadecanone, 1-decalone, 2-decalone, 2-methylcyclohexanone, 3-methylcyclohexanone, 4-methylcyclohexanone, 2,2-dimethylcyclohexanone, 3,3-dimethylcyclohexanone, 4,4-dimethycyclohexanone, 2,6-dimethylcyclohexanone, 2,4-dimethylcyclohexanone, 2,6,6-trimethylcycloheptanone, 3,3,5-trimethylcyclohexanone, and 2,2,6,6-tetramethyl-cyclohexanone.

As used herein, the term "alkoxide" refers to an alkyl-O— group wherein alkyl is as previously described. Exemplary alkoxides include, but are not limited to, methoxide, ethoxide, propoxide, isopropoxide, butoxide, isobutoxide, tert-butoxide, pentoxide, isopentoxide, hexyloxide, and heptyloxide.

The present disclosure is further intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}C$ and $^{14}C$, isotopes of nitrogen include $^{15}N$, and isotopes of oxygen include $^{17}O$ and $^{18}O$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

An aspect of the present disclosure relates to a method of producing a Pt/SrTiO$_3$ photocatalyst comprising strontium titanate nanoparticles and platinum doped on a surface of the strontium titanate nanoparticles. The method comprises (i) mixing a strontium(II) salt with an acid to form a first mixture, (ii) adding a titanium(IV) alkoxide to the first mixture to form a second mixture, (iii) sonicating, drying and calcining the second mixture to form strontium titanate nanoparticles, (iv) mixing a platinum(II) compound with the strontium titanate nanoparticles to form a third mixture, and (v) reducing the third mixture with a reductant to form the Pt/SrTiO$_3$ photocatalyst.

The method includes initially mixing a strontium(II) salt with an acid to form a first mixture. The first mixture may comprise strontium(II) salt at a concentration of 0.1-2 M, preferably 0.2-1 M, more preferably 0.3-0.6 M. The strontium(II) salt may be strontium acetate, strontium carbonate, strontium chloride, strontium bromide, strontium iodide, strontium nitrate, strontium sulfate, strontium hydrogenphosphate, strontium phosphate, strontium hydroxide, and/or some other strontium(II) salts. In one embodiment, more than one type of strontium(II) salt may be used. In a preferred embodiment, the strontium(II) salt is strontium acetate. The first mixture may comprise the acid at a concentration of 0.1-18 M, preferably 1-15 M, preferably 5-12 M. The acid may be an organic acid such as acetic acid, formic acid, propionic acid, benzoic acid, and/or butyric acid. In an alternative embodiment, an inorganic acid, such as hydrochloric acid, sulfuric acid, nitric acid, bromic acid, iodic acid, and/or hydrofluoric acid, may be used in place of the organic acid. In a preferred embodiment, the acid is acetic acid.

The first mixture may be agitated for 0.5-6 hours, preferably 1-4 hours, more preferably 2-3 hours at a temperature of 4-40° C., preferably 10-30° C., more preferably 15-25° C. Methods of agitating a mixture include, without limitation, using an agitator, a vortexer, a rotary shaker, a magnetic stirrer, a centralgal mixer, or an overhead stirrer. In one embodiment, the first mixture is mixed a spatula. In another embodiment, the first mixture is agitated by sonication in an ultrasonic bath or with an ultrasonic probe. In another embodiment, the first mixture is left to stand without being stirred. In a preferred embodiment, the first mixture is agitated using a magnetic stirrer with a rotational speed of at least 250 rpm, preferably at least 400 rpm, more preferably at least 600 rpm.

The method also includes adding a titanium(IV) alkoxide to the first mixture to form a second mixture. The titanium (IV) alkoxide may be added to form a second mixture having a titanium(IV) alkoxide concentration of 1-10 M, preferably 2-8 M, more preferably 4-6 M. The titanium alkoxide may be titanium methoxide, titanium ethoxide, titanium butoxide, titanium propoxide, titanium isopropoxide, titanium pentoxide, titanium tetraethoxide, and/or some other titanium(IV) alkoxides. In one embodiment, more than one type of titanium(IV) alkoxide may be added to form the second mixture. In a preferred embodiment, the titanium(IV) alkoxide is titanium isopropoxide. The second mixture may be agitated using the aforementioned methods for 0.5-12 hours, preferably 2-8 hours, more preferably 4-6 hours at a temperature of 4-40° C., preferably 10-30° C., more preferably 15-25° C. In an preferred embodiment, the second mixture is sonicated at a frequency of vibration of 20-150 kHz, preferably 30-100 kHz, more preferably 40-60 kHz for 0.5-3 hours, preferably 1-2 hours, using a sonication bath or a sonication probe to produce a sonicated mixture. A solvent, e.g. acetone may be added to the second mixture prior to the sonication to facilitate the formation of the sonicated mixture. Alternatively, the second mixture may not be sonicated but instead stirred, shaken, and/or rotated for an equivalent amount of time. In another embodiment, the second mixture may only be mixed to form a homogeneous mixture, and then left to sit for the previously mentioned amount of time.

A solid may form in the sonicated mixture, and the solid may be separated from the liquid phase of the mixture and dried to form a powder. The solid may be isolated by subjecting the sonicated mixture to filtration, centrifugation, evaporation, and/or heated evaporation. The solid may then be dried for 2-48 hours, preferably 8-36 hours, preferably 12-24 hours at a temperature of 60-300° C., preferably 70-200° C., more preferably 80-120° C. In one embodiment, the solid may be dried at these temperatures while being subjected to an absolute pressure of 0.001-10 mbar, 0.01-1 mbar, or 0.1-0.5 mbar. In another embodiment, the solid may be dried at one of the previously mentioned pressures but without heating.

The powder may be calcined for 0.5-12 hours, preferably 1-8 hours, more preferably 3-6 hours, or about 5 hours, at a temperature of 300-600° C., 350-550° C., or 400-500° C. to form strontium titanate nanoparticles. The strontium titanate nanoparticles may be in the same shape or different shapes, and may be the same size or different sizes. The nanoparticles may be spherical, ellipsoidal, oblong, ovoidal, or some other rounded shape in an alternative embodiment, the nanoparticles may be angular, rectangular, prismoidal, or some other angular shape, or they may be nanorods, nanowires, or nanosprings. In a preferred embodiment, the strontium titanate nanoparticles are spherical. The size and shape of particles may be analyzed by techniques such as dynamic light scattering (DLS), scanning electron microscopy (SEM) and/or atomic force microscopy (AFM).

An average diameter (e.g., average particle diameter) of the nanoparticle, as used herein, refers to the average linear distance measured from one point on the nanoparticle through the center of the nanoparticle to a point directly across from it. In one embodiment, the strontium titanate nanoparticles may have an average diameter in a range of 2-50 nm, 3-40 nm, 4-30 nm, or 5-20 nm. In one embodiment, the strontium titanate nanoparticles may be clustered together as agglomerates having an average diameter in a range of 10-500 nm, 50-300 nm, or 100-200 nm. As used herein, the term "agglomerates" refers to a clustered particulate composition comprising primary particles, the primary particles being aggregated together in such a way so as to form clusters thereof, with at least 50 volume percent of the clusters having a mean diameter that is at least 2 times the mean diameter of the primary particles, and preferably at least 90 volume percent of the clusters having a mean diameter that is at least 5 times the mean diameter of the primary particles. In a preferred embodiment, the nanoparticles are well separated from one another and do not form agglomerates. The strontium titanate nanoparticles may be crystalline, polycrystalline, or amorphous. Preferably, the strontium titanate nanoparticles are crystalline. In one embodiment, the strontium titanate nanoparticles have a crystallite size of 5-40 nm, 10-30 nm, or 20-26 nm. In some embodiments, crystallite size is calculated based on X-ray diffraction (XRD) measurement using Scherrer equation [see Example 3].

The Brunauer-Emmet-Teller (BET) theory (S. Brunauer, P. H. Emmett, E. Teller, *J. Am. Chem. Sac,* 1938, 60, 309-319, incorporated herein by reference) aims to explain the physical adsorption of gas molecules on a solid surface and serves as the basis for an important analysis technique for the measurement of a specific surface area of a material. Specific surface area is a property of solids which is the total surface area of a material per unit of mass, solid or bulk volume, or cross sectional area. In most embodiments, BET surface area is measured by gas adsorption analysis, preferably $N_2$ adsorption analysis. In a preferred embodiment, the strontium titanate nanoparticles have a BET surface area of 15-30 $m^2/g$, preferably 17-25 $m^2/g$, more preferably 19-23 $m^2/g$, or about 20 $m^2/g$. The surface may be mesoporous or microporous. The term "microporous" refers to a surface having an average pore diameter of less than 2 nm, while the term "mesoporous" refers to a surface having an average pore diameter of 2-50 nm. An average pore size of the strontium titanate nanoparticles may be in a range of 1-40 nm, 1.2-25 nm, 1.4-10 nm, preferably 1.6-5 nm, more preferably 1.8-2.5 nm.

As used herein, UV-vis spectroscopy or UV-vis spectrophotometry refers to absorption spectroscopy or reflectance spectroscopy in the ultraviolet-visible spectral region. In one or more embodiments, the strontium titanate nanoparticles have an ultraviolet visible absorption with an absorption peak in a range of 350-380 nm, preferably 360-375 nm, preferably 365-370 nm, or about 368 nm. As used herein, photoluminescence (PL) is light emission from any form of matter after the absorption of photons (electromagnetic radiation). In one or more embodiments, the strontium titanate nanoparticles have a photoluminescence peak in a range of 350-410 nm, preferably 360-400 nm, preferably 370-390 nm, or about 380 nm upon excitation at a wavelength of 270-290 nm, preferably 272-288 nm, preferably 274-286 nm, preferably 276-284 nm, preferably 278-282 nm, or about 280 nm.

As used herein, band gap energy, band gap, and/or energy gap refers to an energy range in a solid where no electron states can exist. In graphs of the electronic band structure of solids, the band gap generally refers to the energy difference (in electron volts) between the top of the valence band and the bottom of the conduction band in insulators and/or semiconductors. It is generally the energy required to promote a valence electron bound to an atom to become a conduction electron, which is free to move within the crystal lattice and serve as a charge carrier to conduct electric current. Band gap energies for the $Pt/SrTiO_3$ photocatalyst described herein may be obtained using optical spectroscopies, e.g. UV-vis spectroscopy and/or electrochemical measurements, e.g. cyclic voltammetry (CV) and differential pulse voltammetry (DPV). In one or more embodiments, the strontium titanate nanoparticles have a band gap energy of 3.0-4.5 eV, preferably 3.2-4.0 eV, preferably 3.4-3.8 eV, or about 3.6 eV.

The method further includes mixing the strontium titanate nanoparticles formed above with a platinum(II) compound to form a third mixture. A solvent, e.g. water may be added to the third mixture. The strontium titanate nanoparticles may present in the third mixture at a concentration of 1-100 g/L, 10-80 g/L, 20-70 g/L, 30-60 g/L, or 40-50 g/L. The platinum(II) compound may present in the third mixture at a concentration of 1-2000 mg/L, 10-1500 mg/L, 20-1000 mg L, 30-500 mg/L, or 40-200 mg/L. The platinum(II) compound refers to a salt, complex, and/or a metallo-organic compound comprising platinum(II) ion and one or more counter ions. The platinum(II) compound may or may not comprise additional ligands and may be in any hydration state. Exemplary platinum(II) compounds include, but are not limited to, platinum(II) chloride, platinum(II) bromide, platinum(H) iodide, platinum(II) acetate, platinum(II) acetylacetonate, tetraammineplatinum(II) chloride, tetraammineplatinum(II) nitrate, potassium tetrachloroplatinate(II), sodium tetrachloroplatinate(II), tetraammineplatinum(II) hydroxide, diamminedinitritoplatinum(II), dimethyl(cycloocta-1,5-diene)platinum(II), cis-dichlorobis(triphenylphosphine)platinum(II), dichloro(cycloocta-1,5-diene) platinum(II), potassium trichloro(ethene)platinate(II), dichloro(1,2-diaminocyclohexane)platinum(II). In an alternative embodiment, platinum compounds comprising platinum ions at other oxidation states such as (I), (III), (IV), (V), and/or (VI) may be used in addition to, or in lieu of platinum(II) compounds, such as platinum(IV) oxide, platinum(IV) hydroxide, platinum(IV) sulfide, ammonium hexachloroplatinate, platinum(IV) bromide, platinum(IV) chloride, platinum(IV) fluoride, potassium hexachloroplatinate (IV), sodium hexachloroplatinate(IV), hexachloroplatinic acid(IV), xenon hexafluoroplatinate(V), platinum(V) fluoride, dioxygenyl hexafluoroplatinate(V), and platinum(VI) fluoride. In a preferred embodiment, the platinum(II) compound is platinum(II) chloride.

In one or more embodiment, mixing the platinum(II) compound with the strontium titanate nanoparticles to form the third mixture is conducted under an ultraviolet (UV) light irradiation. As defined herein, ultraviolet light refers to electromagnetic radiation comprising one or more wavelengths within the range 1-400 nm. In one embodiment, the third mixture may additionally be irradiated with light from the visible and/or infrared spectra, for example, light having at least one wavelength in the range of 400 nm-1 mm. Alternatively, an irradiation source may be fitted with a filter to block or attenuate light above 400 nm. The irradiation source may be a flame, a lantern, a gas discharge lamp, an incandescent bulb, a laser, a fluorescent lamp, an electric arc, a light emitting diode (LED), a cathode ray tube, and/or sunlight. The irradiation source may have a total power output of 10-1000 W, 50-750 W, or 100-500 W, and may be positioned 2-30 cm, 5-20 cm, or 10-15 cm from the closest surface of the third mixture. The third mixture may be irradiated with UV light for 0.5-12 hours. 1-6 hours, or 2-4 hours. Preferably the third mixture may be agitated while being irradiated in order to maintain the dispersion of the mixture. However, in one embodiment, the third mixture is not agitated while being irradiated. During irradiation the third mixture may be enclosed in a container and cooled in order to prevent overheating and/or solvent evaporation. Preferably the irradiation of the UV light causes the deposition of platinum onto the surface and/or within a portion of an outer layer of the strontium titanate nanoparticles by incorporating platinum ions within strontium titanate lattice, forming platinum-doped strontium titanate nanoparticles. In some embodiments, the platinum ions may be embedded into the pores of the strontium titanate lattice and thus not integral to the strontium titanate lattice. In another embodiment, the platinum ions are not incorporated into the lattice structure of strontium titanate and may be adsorbed on a surface (e.g. by van der Waals and/or electrostatic forces) of the strontium titanate nanoparticles. In an alternative embodiment, other metals, such as palladium, silver, gold, or a mixture thereof may be used in addition to, or in lieu with platinum for the deposition.

In one embodiment, the platinum-doped strontium titanate nanoparticles are collected from the irradiated third mixture and dried to form a powder. The nanoparticles may be isolated by subjecting the irradiated third mixture to filtration, centrifugation, evaporation, and/or heated evaporation. The nanoparticles may then be dried for 2-48 hours, preferably 8-40 hours, preferably 14-30 hours at a temperature of 30-200° C., preferably 40-150° C., more preferably 50-100° C., or about 60° C. In one embodiment, the nanoparticles may be dried at these temperatures while being subjected to an absolute pressure of 0.001-10 mbar, 0.01-1 mbar or 0.1-0.5 mbar. In another embodiment, the nanoparticles may be dried at one of the previously mentioned pressures but without heating.

In one or more embodiment, the platinum-doped strontium titanate nanoparticles are reduced by a reductant to form the Pt/StTiO$_3$ photocatalyst. In a preferred embodiment, the platinum-doped strontium titanate nanoparticles are treated by hydrogen ($H_2$) at a flow rate of 5-100 mL/min, 10-50 mL/min, or 15-30 mL/min at a temperature of 10-80° C., 25-70° C. or 35-60° C. for 0.5-6 hours, 1-4 hours, or 2-3 hours to form the Pt/StTiO$_3$ photocatalyst. The reduction may be carried out with the presence of a solvent, e.g. methanol, ethanol, isopropanol, toluene. In another embodiment, the reduction is carried out without a solvent. Other exemplary reductant suitable for the present disclosure include, but are not limited to, formaldehyde, hydrazine, tin(II) chloride, sulfate-reducing bacteria, and hydrogenase-displaying yeast.

Figure 2:
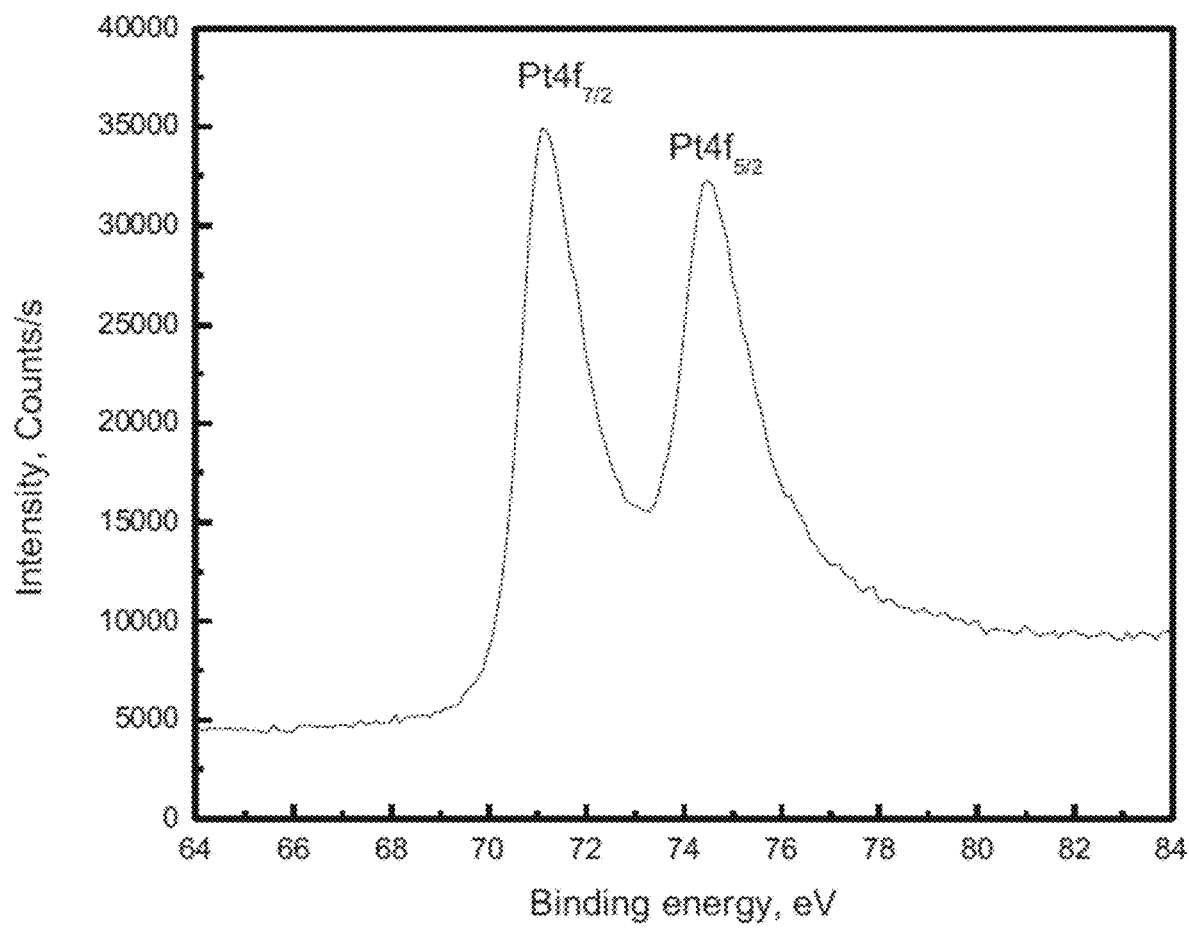
FIG. 2 is an X-ray photoelectron spectroscopy (XPS) spectrum of the $Pt/SrTiO_3$ photocatalyst containing 1.5 wt % of platinum relative to a total weight of the $Pt/SrTiO_3$ photocatalyst.

In one or more embodiments, the formed Pt/StTiO$_3$ photocatalyst comprises 0.1-10 wt %, 0.5-5.0 wt %, 1.0-2.5 wt %, or 1.5-2.0 wt % of platinum relative to a total weight of the Pt/SrTiO$_3$ photocatalyst. In a preferred embodiment, the platinum is in the form of metallic platinum. The presence and dispersity of metallic platinum may be observed by X-ray photoelectron spectroscopy (XPS), transmission electron microscopy (TEM) and high-resolution electron microscopy (HREM). For instance, two peaks of Pt 4f having binding energies of 70.3 eV and 74.0 eV observed in the XPS spectra of Pt/SrTiO$_3$ photocatalyst containing 1.5 wt % of platinum relative to a total weight of the Pt/SrTiO$_3$ photocatalyst [see FIG. 2] are resulted from the presence of metallic platinum in the photocatalyst [Sen F and Gökagaç G 2007. Different sized platinum nanoparticles supported on carbon: an XPS study on these methanol oxidation catalyst J. Phys. Chem. C 111, 5715, incorporated herein by reference in its entirety]. In one embodiment, the formed Pt/StTiO$_3$ photocatalyst comprises 30-60 wt %, 35-55 wt %, 40-50 wt %, or 42-48 wt % of strotium relative to a total weight of the Pt/SrTiO$_3$ photocatalyst. In one embodiment, the formed Pt/StTiO$_3$ photocatalyst comprises 10-35 wt %, 15-32 wt %, 20-30 wt %, or 24-28 wt % of titanium relative to a total weight of the Pt/SrTiO$_3$ photocatalyst. The composition of the Pt/SrTiO$_3$ photocatalyst including weight percentages of platinum, strontium and titanium may be determined by elemental analysis techniques such as energy-dispersive X-ray spectroscopy (EDX), X-ray photoelectron spectroscopy (XPS), inductively coupled plasma mass spectrometry (ICP-MS), and neutron activation analysis.

The Pt/SrTiO$_3$ photocatalyst may be in the form of nanoparticles, which may be in the same shape or different shapes, and may be the same size or different sizes. The nanoparticles may be spherical, ellipsoidal, oblong, ovoidal, or some other rounded shape. In an alternative embodiment, the nanoparticles may be angular, rectangular, prismoidal, or some other angular shape, or they may be nanorods, nanowires, or nanosprings. In one embodiment, the nanoparticles may have an average diameter in a range of 2-50 nm, 3-40 nm, 4-30 nm, or 5-20 nm. In one embodiment, the Pt/SrTiO$_3$ photocatalyst may comprise nanoparticles clustered together as agglomerates having an average diameter in a range of 10-500 nm, 50-300 nm, or 100-200 nm a preferred embodiment, the nanoparticles are well separated from one another and do not form agglomerates. The Pt/SrTiO$_3$ photocatalyst may be crystalline, polycrystalline, or amorphous. Preferably, the Pt/SrTiO$_3$ photocatalyst is crystalline. In one or more embodiments, the Pt/SrTiO$_3$ photocatalyst has a crystallite size of 5-30 nm, 8-20 nm, or 12-18 nm. In certain embodiments, the crystallite size of the Pt/SrTiO$_3$ photocatalyst decreases as the wt % of platinum increases. Such a trend may indicate that platinum doping on the strontium titanate nanoparticle surface could degrade crystallinity of the photocatalyst as a result of local distortion of the crystal structure [Hassan M M, Khan W, Azam A and Naqvi A H 2014. Effect of size reduction on structural and optical properties of ZnO matrix due to successive doping of Fe ions J. Lumin. 145, 160; and Pal M, Pal U, Gracia J M, Jiménez Y and Pérez-Rodriguez F 2012. Effects of crystallization and dopant concentration on the emission behavior of TiO$_2$:Eu nanophosphors Nanoscale Res. Lett. doi:10, 1186/1556-276X-7-1, each incorporated herein by reference in their entirety].

In one or more embodiments, the Pt/SrTiO$_3$ photocatalyst has a BET surface area of 5-30 m$^2$/g, preferably 8-20 m$^2$/g, more preferably 10-18 m$^2$/g, most preferably 10-14 m$^2$/g. The surface may be mesoporous or microporous. In certain embodiments, the BET surface area of the Pt/SrTiO$_3$ photocatalyst decreases as the wt % of platinum increases, which may be attributed to blocking of pores on strontium titanate nanoparticles by the platinum upon doping. It has been surprisingly found that the catalyst activity, in terms of cycloalkane oxidation, increases as the BET surface area of the Pt/SrTiO$_3$ photocatalyst decreases.

In one or more embodiments, the Pt/SrTiO$_3$ photocatalyst has an ultraviolet visible absorption with an absorption peak in a range of 360-380 nm, preferably 365-375 nm, preferably 370-373 nm. In one or more embodiments, the Pt/SrTiO$_3$ photocatalyst has a photoluminescence peak in a range of 380-480 nm, preferably 400-460 nm, preferably 410-440 nm, preferably 420-430 nm upon excitation at a wavelength of 270-290 nm, preferably 272-288 nm, preferably 274-286 nm, preferably 276-284 nm, preferably 278-282 nm, or about 280 nm. In one or more embodiments, the Pt/SrTiO$_3$ photocatalyst has a band gap energy of 2.5-3.6 eV, preferably 2.6-3.4 eV, preferably 2.7-3.2 eV, preferably 2.8-3.0 eV.

Another aspect of the present disclosure relates to a process of oxidizing a cycloalkane to a cycloalkanol and/or a cycloalkanone. The process involves contacting a feed mixture comprising the cycloalkane and an oxidant with a Pt/SrTiO$_3$ photocatalyst thereby forming a reaction mixture, and concurrently irradiating the reaction mixture with light thereby forming the cycloalkanol and/or the cycloalkanone, wherein the Pt/SrTiO$_3$ photocatalyst comprises strontium titanate nanoparticles and platinum doped on a surface of the strontium titanate nanoparticles, in which the platinum is present in an amount of 0.1-5.0 wt % relative to a total weight of the Pt/SrTiO$_3$ photocatalyst.

The Pt/SrTiO$_3$ photocatalyst used in the process may have properties such as composition, crystallite size, surface area, absorption and emission profiles, and band gap energy, as previously described. Preferably, the Pt/SrTiO$_3$ photocatalyst used here may have a crystallite size of 5-30 nm, 8-20 nm, or 12-18 nm, a BET surface area of 5-25 m$^2$/g, preferably 10-20 m$^2$/g, more preferably 14-18 m$^2$/g, an ultraviolet visible absorption with an absorption peak in a range of 360-380 nm, preferably 365-375 nm, preferably 370-373 nm, a band gap energy of 2.5-3.6 eV, preferably 2.6-3.4 eV, preferably 2.7-3.2 eV, preferably 2.8-3.0 eV, and a photoluminescence peak in a range of 380-480 nm, preferably 400-460 nm, preferably 410-440 nm, preferably 420-430 nm upon excitation at a wavelength of 270-290 nm, preferably 272-288 nm, preferably 274-286 nm, preferably 276-284 nm, preferably 278-282 nm, or about 280 nm. In one or more embodiments, the Pt/SrTiO$_3$ photocatalyst is produced as described previously and may comprise 0.1-10 wt %, preferably 0.5-5.0 wt %, preferably 1.0-2.5 wt %, preferably 1.5-2.0 wt % of platinum relative to a total weight of the Pt/SrTiO$_3$ photocatalyst. In one embodiment, the strontium titanate nanoparticles may be pre-formed, or synthesized by a method different than the method described in the previous aspect such as hydrothermal method and sol-gel technique. In another embodiment, the strontium titanate nanoparticles are not preformed, and are synthesized from a titanium alkoxide by sonication as described previously. Strontium titanate nanoparticles may be doped with platinum by the aforementioned photo-assisted deposition method or by a different method such as atomic layer deposition, sputtering, deposition-precipitation, and ion-exchange technique. In another embodiment, strontium titanate nanoparticles may be doped with a different metal, such as palladium, silver, gold, or a mixture thereof.

In one or more embodiments, the cycloalkane is present in the feed mixture at a concentration of 10-400 ppm, preferably 25-350 ppm, preferably 50-300 ppm, preferably 100-250 ppm, or about 200 ppm. In one or more embodiments, the oxidant is present in an amount of 5-30 vol. %, preferably 6-25 vol. %, preferably 7-20 vol. %, preferably 8-15 vol. %, or about 10 vol. % relative to a total volume of the feed mixture. In a preferred embodiment, the oxidant is O$_2$. Other oxidants useful for the present disclosure include, but are not limited to, air, inorganic peroxides such as hydrogen peroxide, sodium peroxide, and barium peroxide, and organic peroxides such as tell-butyl hydroperoxide, cumene hydroperoxide, dicumyl peroxide, tert-butyl peroxide, and tert-butyl peroxybenzoate.

In one or more embodiments, the feed mixture further comprises an inert gas such as N$_2$, Ar, He. In a preferred embodiment, a N$_2$ stream at a feed rate of 10-50 L/h, 20-40 L/h, or about 30 L/h is mixed with the oxidant (e.g. O$_2$) before the oxidizing process. In another embodiment, the inert gas may be bubbled in the feed mixture in a sealed container for at least 0.5 hour, 1 hour, or at least 2 hours before the oxidizing process.

In one or more embodiments, the feed mixture further comprises water. The water may be tap water, distilled water, bidistilled water, deionized water, deionized distilled water, reverse osmosis water, and/or some other water. In one embodiment the water is bidistilled to eliminate trace metals. Preferably the water is bidistilled, deionized, deionized distilled, or reverse osmosis water and at 25° C. has a conductivity at less than 10 μS·cm$^{-1}$, preferably less than 1 μS·cm$^{-1}$, a resistivity greater than 0.1 MΩ·cm, preferably greater than 1 MΩ·cm, more preferably greater than 10 MΩ·cm, a total solid concentration less than 5 mg/kg, preferably less than 1 mg/kg, and a total organic carbon concentration less than 1000 μg/L, preferably less than 200 μg/L, more preferably less than 50 μg/L. Preferably the water is bidistilled, deionized, deionized distilled, or reverse osmosis water. In one embodiment, the water is present in the feed mixture at a concentration of 50-700 ppm, preferably 100-600 ppm, preferably 200-500 ppm, preferably 300-400 ppm, or about 320 ppm.

In one or more embodiments, the feed mixture is contacted with the Pt/SrTiO$_3$ photocatalyst to form a reaction mixture. In a preferred embodiment, the Pt/SrTiO$_3$ photocatalyst is present at a concentration of 0.2-5.0 g per liter of the reaction mixture during the contacting, preferably 0.5-4.0 g/L, preferably 0.8-3.0 g/L, preferably 1.0-2.0 g L$^{-1}$, or about 1.2 g per liter of the reaction mixture during the contacting.

In a preferred embodiment, the feed mixture is contacted with the Pt/SrTiO$_3$ photocatalyst at a pressure of 0.3-4 atm, preferably 0.5-2 atm, preferably 0.75-1.5 atm, or about 1 atm. In a preferred embodiment, the feed mixture is contacted with the Pt/SrTiO$_3$ photocatalyst at a temperature of 30-90° C., preferably 40-80° C., preferably 50-70° C., or about 60° C.

The aforementioned reaction mixture may be concurrently irradiated with light for 0.5-6 hours, preferably 0.75-4 hours, preferably 1-3 hours, or about 1.5 hours. The light may be visible light having a wavelength of 400-800 nm. The light may comprises one or more wavelengths within the range of 400-800 nm. Preferably an irradiation source is used which emits a broad wavelength range of light and which comprises a portion or the entire visible light spectrum. An irradiation source may additionally emit light of wavelengths below 400 nm and/or above 800 nm. In one embodiment, a filter may be used to prevent UV light from entering the reaction mixture, for example, a filter that blocks light with wavelengths less than 420 nm may be used with a xenon or mercury gas discharge lamp. In another embodiment, a solution of 2 M $NaNO_3$ may be placed between the reaction mixture and the irradiation source to attenuate or block light with wavelengths below 400 nm while letting visible light pass through. Alternatively, an irradiation source may be used which only emits light within the visible spectrum. The irradiation source may emit a total power of 50-1000 W, preferably 100-750 W, more preferably 250-500 W, or about 300 W, and may be positioned 2-30 cm, preferably 5-20 cm, more preferably 8-15 cm from the closest surface of the reaction mixture.

The oxidizing process may be carried out in vessels, tanks, containers, or small scale applications in both batch mode and continuous process (e.g. fixed-bed and fluidized-bed modes) reactors. As used herein, "continuous" refers to a process used to produce materials without interruption or where the reactants are flowed and/or in motion during the reaction. In a preferred embodiment, a reactor with a transparent window is used. For example, the window may comprise glass or quartz, though in one embodiment, a polymeric material transparent to visible light and chemically stable with the reaction mixture may be used. As defined herein, "transparent" refers to an optical quality of a compound wherein a certain wavelength or range of wavelengths of light may traverse through a portion of the compound with a small loss of light intensity. Here, the "transparent window" may causes a loss of less than 10%, preferably less than 5%, more preferably less than 2% of the intensity of a certain wavelength or range of wavelengths of light. In one embodiment, the reactor wall and window may comprise the same material, for example, a reactor may comprise quartz walls, which may also function as transparent windows. In some embodiments, the $Pt/SrTiO_3$ photocatalyst is dispersed within the reaction mixture. In another embodiment, the $Pt/SrTiO_3$ photocatalyst may be present as a coating having an average thickness of 0.001-1 mm, 0.01-0.5 mm, 0.05-0.4 mm, or 0.1-0.3 mm on an interior surface of a reactor. In a preferred embodiment, the $Pt/SrTiO_3$ photocatalyst is mixed with a glass or quartz support at a weight ratio of about 1:50 to about 1:1, preferably about 1:25 to about 1:4, preferably about 1:15 to about 1:10, and then used as a photocatalyst in the reaction mixture. The reaction mixture may be agitated using methods described previously while being irradiated, though in one embodiment, the reaction mixture is left to sit while irradiating. In an alternative embodiment, the reaction mixture may be irradiated with UV light, or without visible light. In another alternative embodiment, the reaction mixture may be subjected to different temperatures and pressures than ones described herein, and/or an electric current in order to catalyze the oxidation of the cycloalkane to the cycloalkanol and/or cycloalkanone.

Photocatalytic oxidations often start from separation of photogenerated electron-hole pairs, which may lead to formation of intermediate radicals such as hydroxyl radicals (.OH) in the presence of molecular oxygen and/or peroxides. It was reported that $Al_2O_3$, $TiO_2$ and $ZrO_2$ doped with Pt exhibited oxidative activity of cyclohexane to cyclohexanone and cyclohexanol [Hammoumraoui I R, Braham A C, Roy L P and Kappenstein C 2011, Catalytic oxidation of cyclohexane to cyclohexanone and cyclohexanol by tert-butyl hydroperoxide over Pt/oxide catalysts Bull. Mater. Sci. 34, 1127, incorporated herein by reference in its entirety]. In terms of the present disclosure, radical species may interact with reactants e.g. cycloalkanes in the reaction mixture to form oxidized alcohol and more oxidized ketone derivatives. Factors contributing to the enhancement of the catalytic activity of the doped $Pt/SrTiO_3$ photocatalyst compared to the bare $SrTiO_3$ nanoparticles include (i) prevention of the recombination of electron-hole pairs by Pt atoms in $Pt/SrTiO_3$ photocatalysts, as the doped metal atoms often act as electron traps [Mohamed R M, McKinney D L and Sigmund W M 2012. Enhanced nanocatalysts Mater. Sci. Eng. R 73, 1, incorporated herein by reference in its entirety], (ii) a decrease of band gap energy which allows absorption of photons in the visible region and (iii) promotion of interfacial electron transfer process as Pt atoms lead to formation of Schottky barriers on the $SrTiO_3$, which function as electron traps and facilitate electron-hole separation. In a preferred embodiment, irradiation of the reaction mixture may induce the $Pt/SrTiO_3$ photocatalyst to photocatalytically convert the cycloalkane to a cycloalkanol and/or a cycloalkanone. Preferably the photocatalytic conversion oxidizes one or more alkyl functionalities of the cycloalkane to hydroxyl or ketone groups, though in an alternative embodiment, other reactions may occur. In a preferred embodiment, the oxidation process has a molar conversion of the cycloalkane to the cycloalkanol and/or the cycloalkanone of greater than 40%, preferably greater than 60%, preferably greater than 70%, preferably greater than 80%, preferably greater than 90%, preferably greater than 95%. In one embodiment, a mixture of different cycloalkanes may be converted to a mixture of different cycloalkanols and different cycloalkanones. In an alternative embodiment, the $Pt/SrTiO_3$ photocatalyst may catalyze a cycloalkane to a cycloalkanol and/or a cycloalkanone without light irradiation but with high temperature, high pressure, and/or an electric current.

In one or more embodiments, the platinum is present in an amount of 1.3-3.0 wt %, preferably 1.4-2.0 wt %, or about 1.5 wt % relative to a total weight of the $Pt/SrTiO_3$ photocatalyst, the reaction mixture is irradiated with the light for 1 to 4 hours, preferably 1.2 to 3 hours, or about 1.5 hours, and the process has a molar conversion of the cycloalkane to the cycloalkanol and/or cycloalkanone of greater than 95%, preferably greater than 96%, preferably greater than 97%, preferably greater than 98%, preferably greater than 99%, preferably greater than 99.5%.

In one or more embodiments, the cycloalkane is cyclohexane, the cycloalkanol is cyclohexanol and the cycloalkanone is cyclohexanone. In one embodiment, the formed cycloalkanol and/or the cycloalkanone remain in the reaction mixture but may be quantified by gas chromatography (GC) and/or liquid chromatography (LC). In an alternative embodiment, the formed cycloalkanol and/or the cycloalkanone may be separated from the reaction mixture and purified. In one embodiment, a mixture of cycloalkanol and cycloalkanone is formed at a molar ratio of 100:1 to 1:100, preferably 50:1 to 1:50, preferably 10:1 to 1:10, preferably 5:1 to 1:5 during the oxidizing process. In an alternative embodiment, only cycloalkanol is formed during the process. In another embodiment, only cycloalkanone is formed during the process. The identity and ratio of the isolated cycloalkanol and cycloalkanone may be analyzed by nuclear magnetic resonance (NMR) spectroscopy, infrared (IR) spectroscopy, high-performance liquid chromatography (HPLC), and/or gas chromatography (GC).

In one or more embodiments, the process further comprises recovering the $Pt/SrTiO_3$ photocatalyst after the irradiating to obtain a recovered $Pt/SrTiO_3$ photocatalyst, and reusing the recovered Pt/SrTiO₃ photocatalyst. The recovered Pt/SrTiO₃ photocatalyst may maintain photocatalytic activity for at least 4, preferably at least 8, preferably at least 12 reaction cycles. The recovering may or may not require washing and/or drying between reaction cycles. As defined herein, "maintaining photocatalytic activity" means that when recycling and reusing the recovered Pt/SrTiO₃ photocatalyst, the photocatalytic activity of forming the cycloalkanol and/or the cycloalkanone e.g. measured as the aforementioned molar conversion of the cycloalkane to the cycloalkanol and/or cycloalkanone) remains within at least 90%, preferably at least 95%, more preferably at least 96% of its original value.

The examples below are intended to further illustrate protocols for preparing and characterizing Pt/SrTiO₃ photocatalyst, and assessing the method of oxidizing a cycloalkane to a cycloalkanol and/or a cycloalkanone using the Pt/SrTiO₃ photocatalyst. They are not intended to limit the scope of the claims.

Example 1

Photocatalyst Preparation

Strontium titanate (SrTiO₃) nanoparticles were prepared by an ultrasonic method. 0.3 mole of strontium acetate was added under a nitrogen atmosphere to 16 mol glacial acetic acid and stirred for 2 h at room temperature. Then, 5 mol titanium isopropoxide was added to the solution mentioned above and the resulting mixture was stirred at room temperature for 6 h. Then, 20 mL of acetone was added and the resulting mixture was put in an apparatus for low-frequency ultrasound (Bransonic 42 kHz) for 1 h. The resulting material was dried at 100° C. for 24 h, then calcined at 550° C. for 5 h in air. A photo-assisted deposition (PAD) route was used to prepare Pt/SrTiO₃ photocatalysts which contain different wt % of Pt metal (0.5, 1.0, 1.5 and 2.0 wt %). In this route, Pt metal was deposited on SrTiO₃ nanoparticles using an aqueous solution of platinum chloride while applying UV light irradiation. The obtained samples were dried at 60° C. for 24 h and treated with H₂ (20 mL min⁻¹) at 60° C. for 2 h.

Example 2

Photocatalyst Characterization

The crystalline phase of the strontium titanate (SrTiO₃) nanoparticles and Pt/SrTiO₃ photocatalysts was determined using powder X-ray diffraction (XRD) (Bruker axis D8 instrument) using CuKα radiation (λ=1,540 Å) in the 2θ range from 10° to 80° at room temperature. The chemical state information of the photocatalysts was determined using X-ray photoelectron spectroscopy (XPS) (Thermo Scientific K-ALPHA spectrometer). The morphological structure of the strontium titanate (SrTiO₃) nanoparticles and Pt/SrTiO₃ photocatalysts was examined using a transmission electron microscope (TEM) (JEOL-JEM-1230). Specimens for TEM analysis were prepared by dispersing the nanoparticles in ethanol and placing one drop onto a holey-carbon-coated copper supported grid. The specific surface area was determined from nitrogen adsorption/desorption isotherms which were measured at 77 K using a Nova 2000 series Chromatech. Prior to the analysis, the samples were outgassed at 150° C. for 24 h. UV-Vis-NIR spectrophotometer (V-570, Jasco, Japan) equipped with a standard cell for solid materials (Jasco, Japan) was used to estimate the band gap energy in air at room temperature by measuring ultra violet-visible diffuse reflectance (UV-Vis-DRS) spectra over the range of 200 to 800 nm. Shimadzu RF-5301 fluorescence spectrophotometer was used to measure the photoluminescence emission spectra (PL).

Example 3

Characterization of Strontium Titanate Nanoparticles and Pt SrTiO₃ Photocatalysts FIG. 1 illustrates XRD patterns of the strontium titanate (SrTiO₃) nanoparticles and Pt/SrTiO₃ photocatalysts. The obtained XRD patterns of the strontium titanate (SrTiO₃) nanoparticles and Pt/SrTiO₃ photocatalysts reveal characteristic peaks of SrTiO₃, suggesting that doping strontium titanate nanoparticles with Pt does not significantly affect their structure. Furthermore, the characteristic XRD peaks of platinum or platinum oxide were not detected, which could be attributed to the fact that the weight percent platinum was lower than the detection limit and/or good dispersion of Pt on the SrTiO₃ nanoparticles surface was achieved. The same phenomenon was observed when oxomolybdate species dispersed over TiO₂ which was used for direct methanol oxidation [Faye J. Capron M. Takahashi A, Paul S. Katryniok B, Fujitani T and Dumeignil F 2015. Effect of dispersion on to dimethoxymethane over MoOx/TiO₂ Energy Sci Eng. 3, 115, incorporated herein by reference in its entirety].

In addition, it was observed that the intensity of the characteristic SrTiO₃ peak decreased as the weight percentage of doped platinum increased, especially at 32.15°. Scherer equation was used to calculate the crystallite size based on the half-width of the most intense peak at 2θ=32.15°. The calculated crystallite size were 24.0, 20.0, 17.0, 14.0 and 12.0 nm for SrTiO₃, 0.5 wt % Pt/SrTiO₃, 1.0 wt % Pt/SrTiO₃, 1.5 wt % Pt/SrTiO₃ and 2.0 wt % Pt/SrTiO₃, respectively.

Figure 3A:
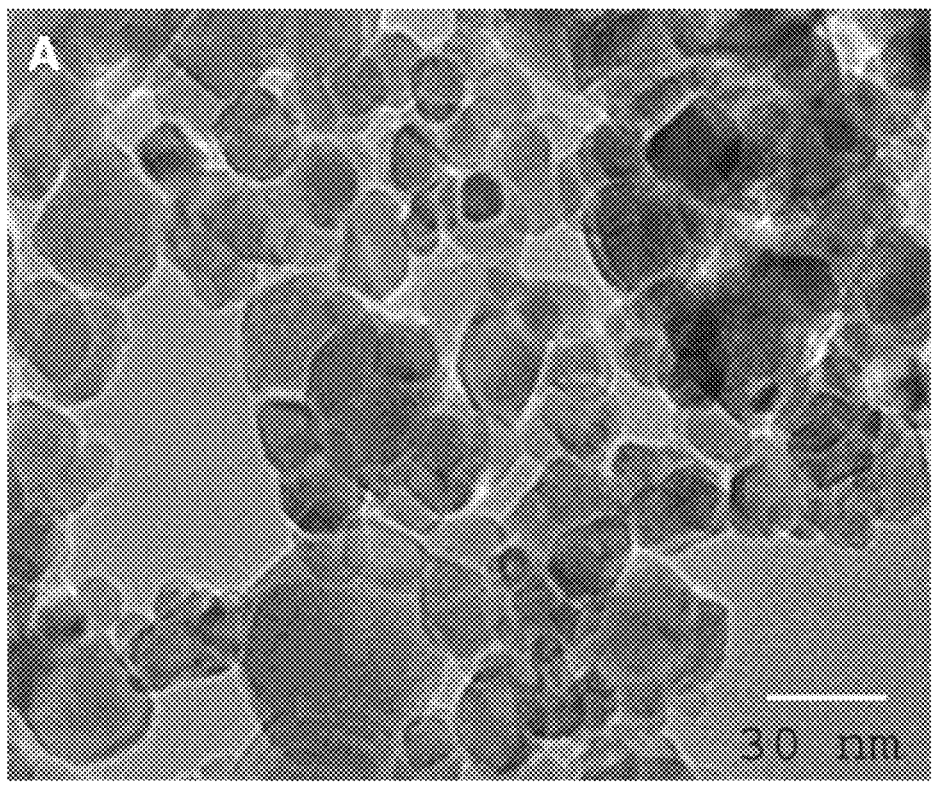
FIG. 3A is a transmission electron microscope (TEM) image of strontium titanate nanoparticles ($SrTiO_3$).
Figure 3B:
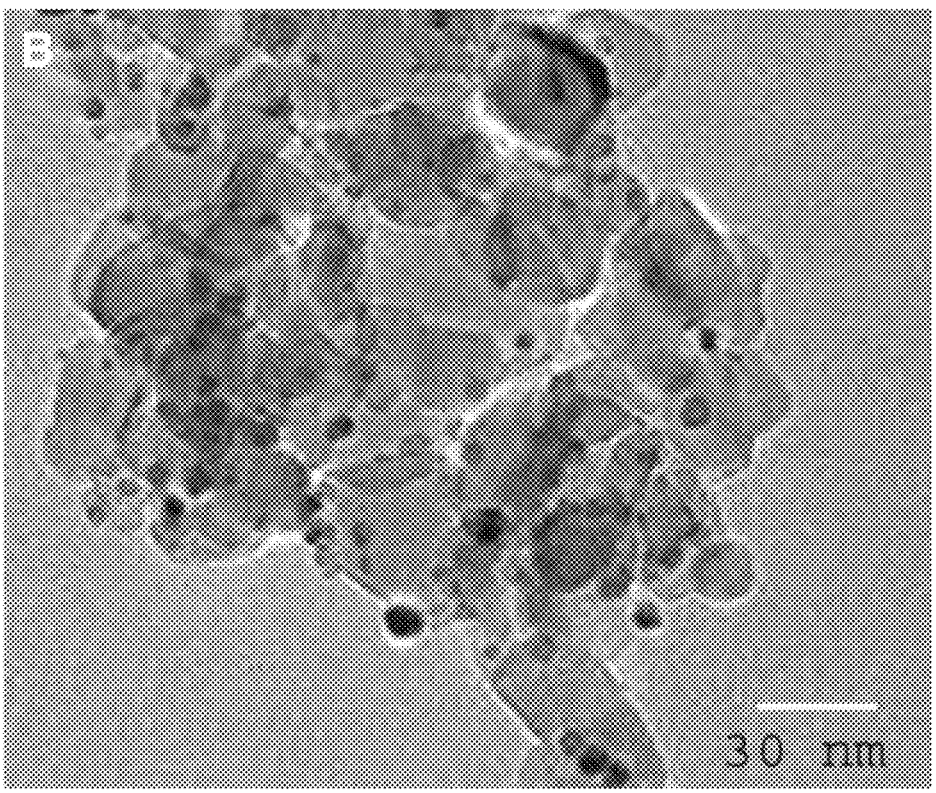
FIG. 3B is a TEM image of the $Pt/SrTiO_3$ photocatalyst containing 1.5 wt % of platinum relative to a total weight of the $Pt/SrTiO_3$ photocatalyst.

FIGS. 3A and 3B are TEM images of SrTiO₃ and 1.5 wt % Pt/SrTiO₃ photocatalyst. These images demonstrate that SrTiO₃ is a spherical nanoparticle as shown in FIG. 3A and platinum was doped as dots as shown in FIG. 3B. Table 1 summarizes BET specific surface area of SrTiO₃ nanoparticles and Pt/SrTiO₃ photocatalysts calculated according to the BET adsorption isotherm model. The calculated BET surface area were 20, 18, 16, 14 and 10 m²/g for SrTiO₃, 0.5 wt % Pt/SrTiO₃, 1.0 wt % Pt/SrTiO₃, 1.5 wt % Pt/SrTiO₃, and 2.0 wt % Pt/SrTiO₃, respectively.

TABLE 1

BET surface area of SrTiO3 and Pt-doped SrTiO3 nanoparticles

| Sample | $S_{BET}$ (m²/g) |
|---|---|
| SrTiO₃ | 20 |
| 0.5 wt % Pt doped SrTiO₃ | 18 |
| 1.0 wt % Pt doped SrTiO₃ | 16 |
| 1.5 wt % Pt doped SrTiO₃ | 14 |
| 2.0 wt % Pt doped SrTiO₃ | 10 |

Figure 4:
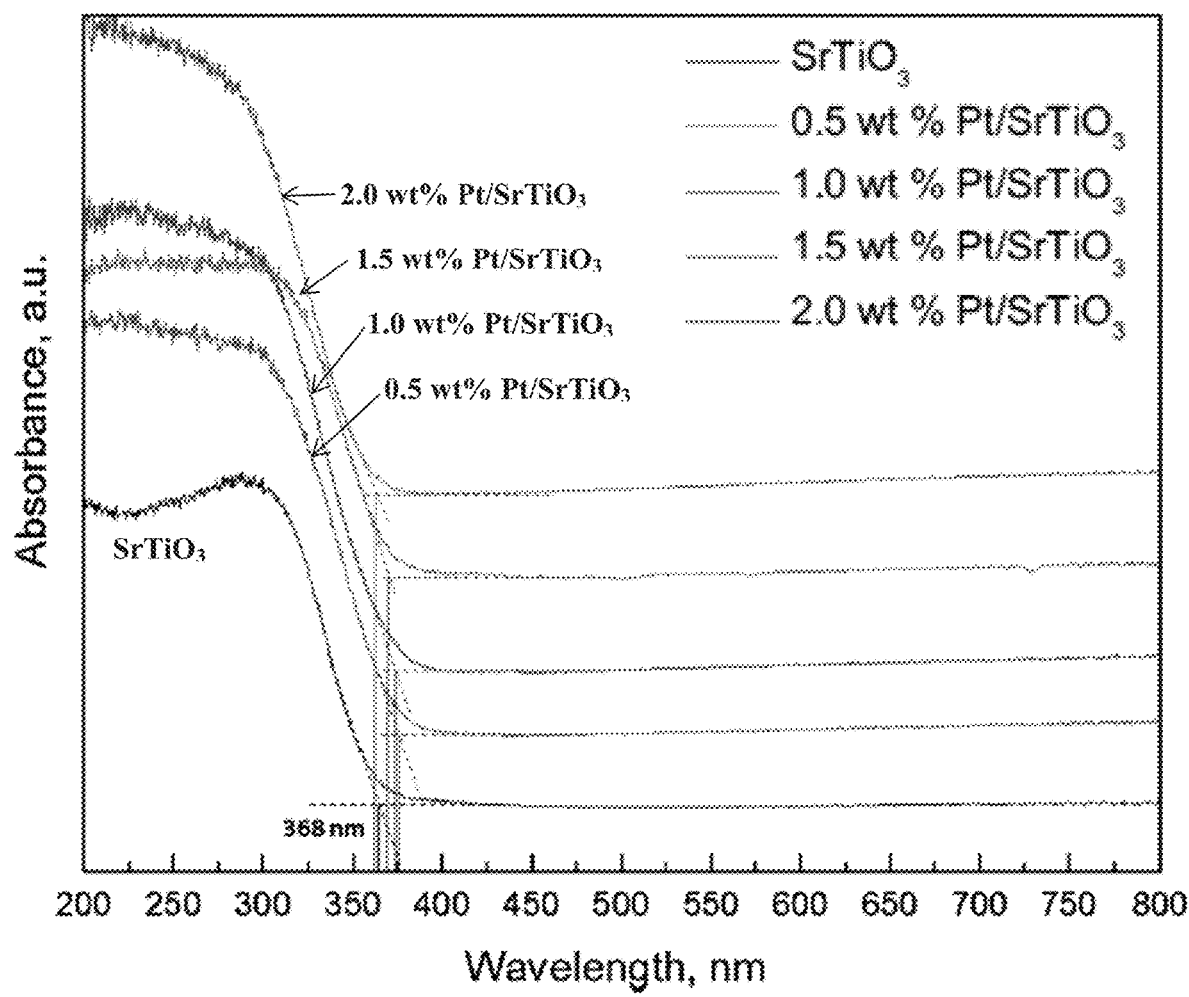
FIG. 4 is an overlay of the UV-vis absorption spectra of strontium titanate nanoparticles ($SrTiO_3$), and $Pt/SrTiO_3$ photocatalysts containing 0.5 wt % (0.5 wt % $Pt/SrTiO_3$), 1.0 wt % (1.0 wt % $Pt/SrTiO_3$), 1.5 wt % (1.5 wt % $Pt/SrTiO_3$), and 2.0 wt % (2.0 wt % $Pt/SrTiO_3$) of platinum relative to a total weight of each $Pt/SrTiO_3$ photocatalyst.
Figure 5:
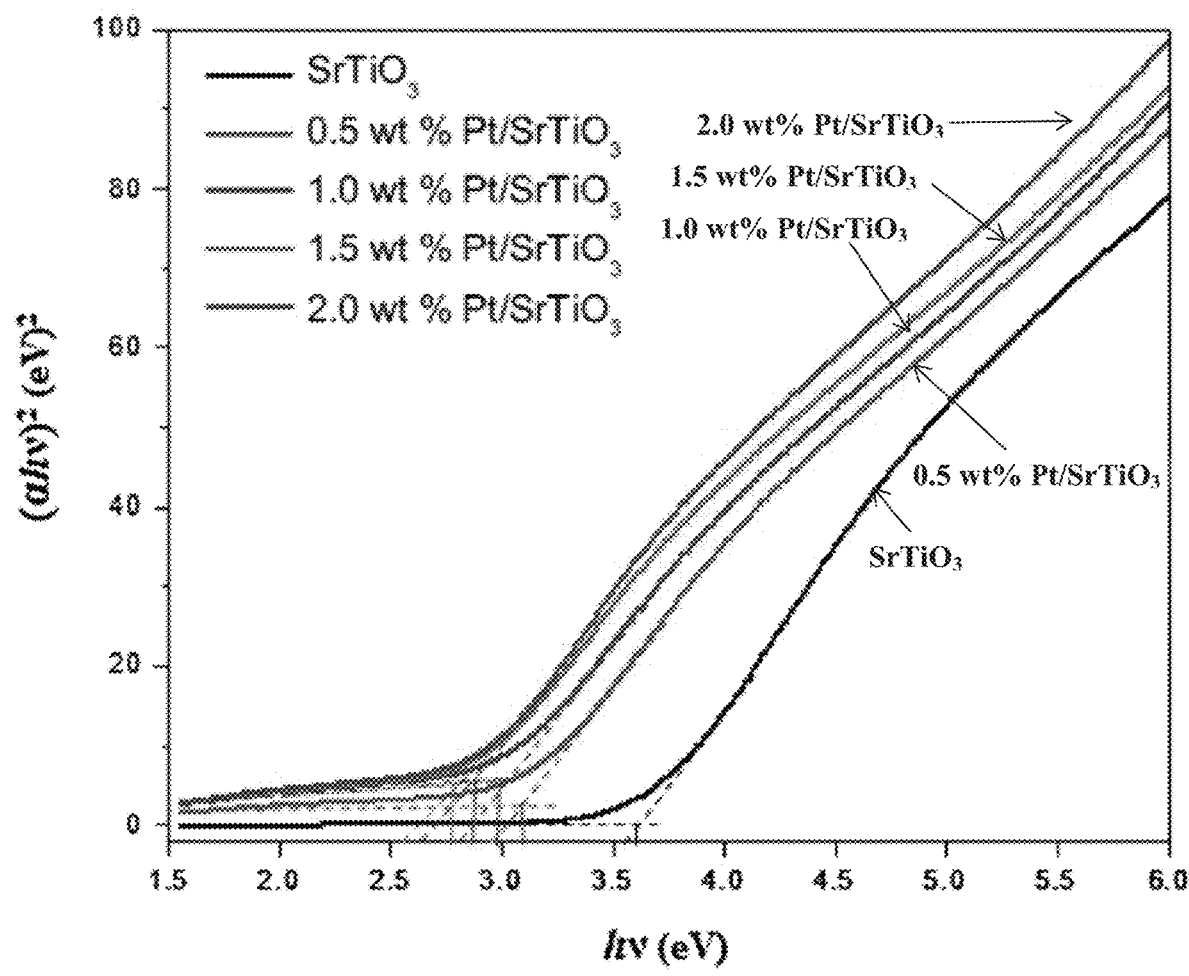
FIG. 5 is an overlay of the band gap energy calculations for strontium titanate nanoparticles ($SrTiO_3$), and $Pt/SrTiO_3$ photocatalysts containing 0.5 wt % (0.5 wt % $Pt/SrTiO_3$), 1.0 wt % (1.0 wt % $Pt/SrTiO_3$), 1.5 wt % (1.5 wt % $Pt/SrTiO_3$), and 2.0 wt % (2.0 wt % $Pt/SrTiO_3$) of platinum relative to a total weight of each $Pt/SrTiO_3$ photocatalyst.

FIG. 4 demonstrates UV-Vis-DRS spectra of SrTiO₃ nanoparticles and Pt/SrTiO₃ photocatalysts. The results reveal that SrTiO₃ nanoparticles absorb the UV region (368 nm). However, the absorption peaks of Pt/SrTiO₃ photocatalysts were shifted to longer wavelength (~375 nm, ~373 nm, ~370 nm, and ~366 nm for 0.5 wt % Pt/SrTiO₃, 1.0 wt % Pt/SrTiO₃, 1.5 wt % Pt/SrTiO₃, and 2.0 wt % Pt/SrTiO₃, respectively). Similar trend was observed earlier when titania nanotubes were doped with Pt [Vijayan B K, Dimitrijevic N M, Wu J and Gray K A 2010. The effects of Pt doping on the structure and visible light photoactivity of titania nanotubes J. Phys. Chem. C 114, 21262, incorporated herein by reference in its entirety]. The band gap (Eg) for $SrTiO_3$ and $Pt/SrTiO_3$ photocatalysts was calculated from the UV-Vis-DRS spectra by using Tauc's relation [Chrysicopoulou P, Davazoglou D, Trapalis C and Kordas G 1998 Photocatalytic destruction of methylene blue on $Ag@TiO_2$ with core/shell structure Thin Solid Films 323, 188, incorporated herein by reference in its entirety]:

$$\alpha h\nu = B(h\nu - E_g)^n$$

where α is the optical absorption coefficient, E (=hc/λ) is the photon energy, B is a constant, λ is the measured wavelength in nm, $E_g$ is the optical band gap, and n is ½ or 2 for direct or indirect band gap semiconductor, respectively. FIG. 5 shows the linear part of the plot of $((\alpha h\nu)^2$ vs. αh, while $E_g$ values were estimated by extrapolating each plot to its baseline which were presented in Table 2. It is clear that band gap energy for Pt-doped photocatalysts are smaller than those for $SrTiO_3$ nanoparticles, and the band gap energy values can be tuned by weight percentage of the doped Pt.

TABLE 2

Band gap energies of $SrTiO_3$ arid Pt-doped $SrTiO_3$ nanoparticles ($Pt/SrTiO_3$ photocatalysts)

| Sample | Band gap energy eV |
| --- | --- |
| $SrTiO_3$ | 3.60 |
| 0.5 wt % Pt doped $SrTiO_3$ | 3.10 |
| 1.0 wt % Pt doped $SrTiO_3$ | 2.98 |
| 1.5 wt % Pt doped $SrTiO_3$ | 2.85 |
| 2.0 wt % Pt doped $SrTiO_3$ | 2.75 |

Figure 6:
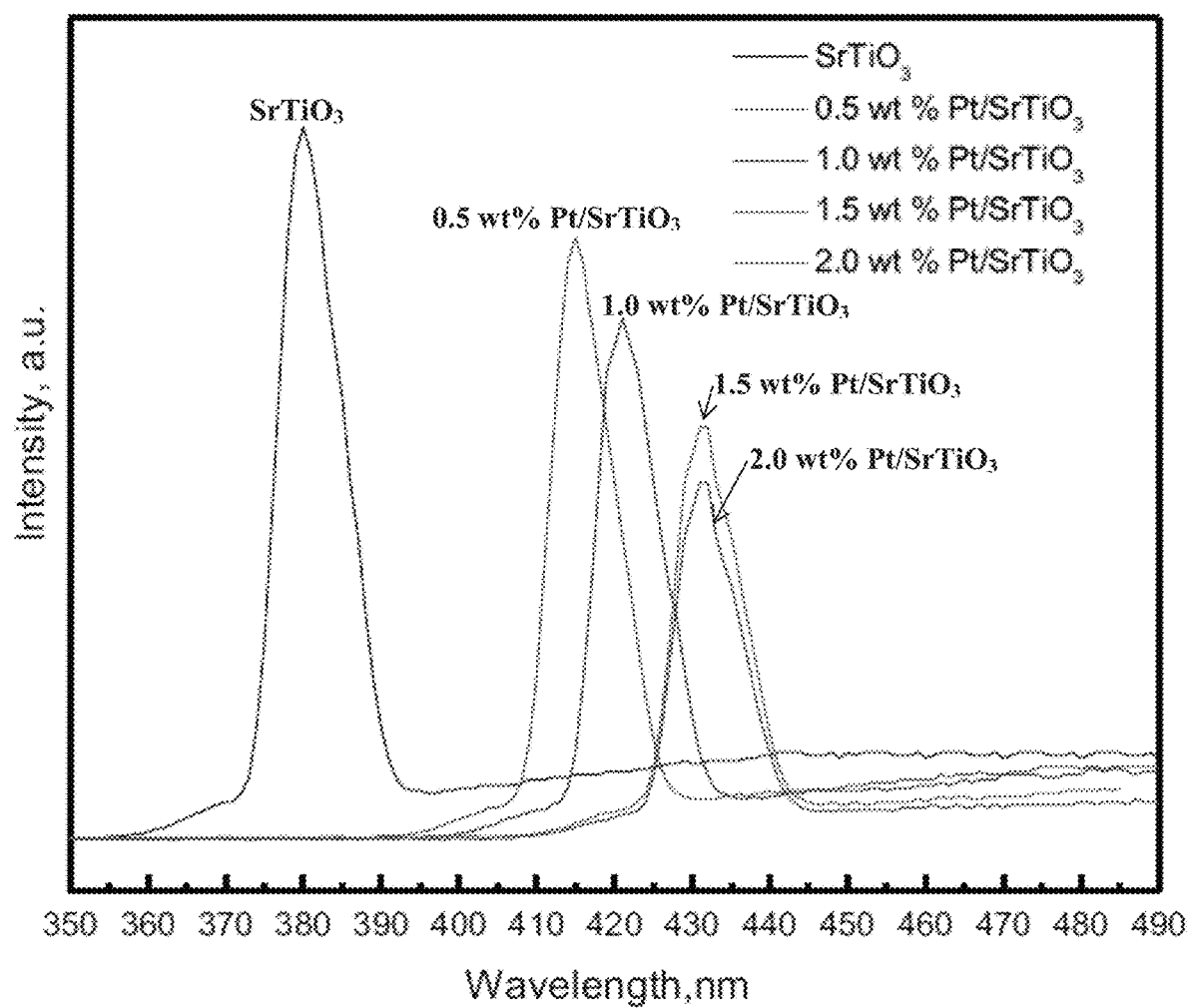
FIG. 6 is an overlay of the photoluminescence (PL) emission spectra of strontium titanate nanoparticles ($SrTiO_3$), and $Pt/SrTiO_3$ photocatalysts containing 0.5 wt % (0.5 wt % $Pt/SrTiO_3$), 1.0 wt % (1.0 wt % $Pt/SrTiO_3$), 1.5 wt % (1.5 wt % $Pt/SrTiO_3$), and 2.0 wt % (2.0 wt % $Pt/SrTiO_3$) of platinum relative to a total weight of each $Pt/SrTiO_3$ photocatalyst.

FIG. 6 illustrates the PL spectra of the $SrTiO_3$ and $Pt/SrTiO_3$ photocatalysts. The results show that peak intensity of the PL for $SrTiO_3$ reduced as the Pt weight percentage increased from 0 to 1.5%, however, no further enhancement of peak intensity was observed beyond the Pt weight percentage at 1.5%, indicating the significant effect of doping $SrTiO_3$ with Pt by influencing the rate of the electron-hole recombination. This observation may be due to the formation of Schottky barriers on the $SrTiO_3$ upon Pt deposition, which might serve as electron traps. These electron traps would facilitate the electron-hole separation and promote the interfacial electron transfer process, thus make the photocatalyst more efficient [Grabowska E, Marchelek M, Klimczuk T, Lisowski W and Zaieska-Medynska A 2017, $TiO_2/SrTiO_3$ and $SrTiO_3$ microspheres decorated with Rh, Ru or Pt nanoparticles: Highly UV-vis responsible photoactivity and mechanism J. Catal. 350, 159, incorporated herein by reference in its entirety].

Example 4

Photocatalytic Oxidation of Cyclohexane: Experimental

Photocatalytic experiments were performed by feeding a $N_2$ stream at 30 L/h (STP) containing 200 ppm cyclohexane, 10 vol. % $O_2$ at a temperature of 60° C. and a reaction pressure of 1 atm. Nitrogen functioned as the carrier gas for cyclohexane. Additionally, 320 ppm of water vaporized from 60° C. controlled saturators was added in order to minimize photodeactivation of the catalyst. A fluidized bed photoreactor was used as the reactor, which was irradiated by a Xenon lamp covered by a cut-off filter of 420 nm with a power of 300 W and an intensity of 0.96 W/cm². The catalytic bed was composed of 1.2 g of photocatalyst mixed with 20 g glass spheres in order to improve the fluidization property. The reactor inlet reactants and outlet products were analyzed using gas chromatography (Agilent GC 7890A model). The reactor was irradiated after complete adsorption of cyclohexane on the catalyst surface. The photocatalytic behavior of all analyzed samples was evaluated as:

$$X = (C_0 - C_1)/C_0 \times 100\%$$

where X=cyclohexane conversion, $C_0$=inlet cyclohexane concentration, and $C_1$=outlet cyclohexane concentration.

Example 5

Photocatalytic Oxidation of Cyclohexane: Results and Discussion

Figure 7:
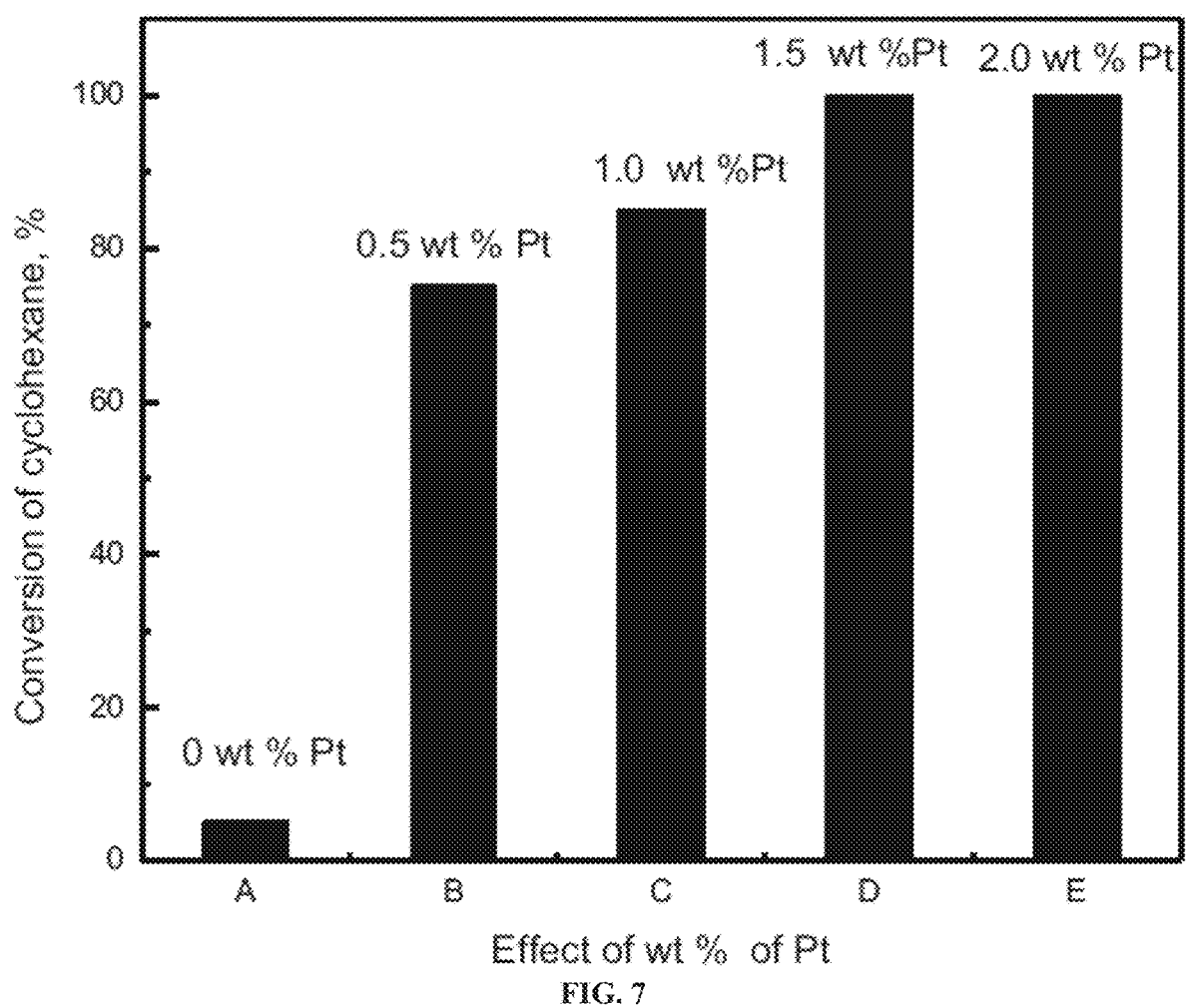
FIG. 7 is a graph showing the photocatalytic activity of strontium titanate nanoparticles (0 wt % Pt), and $Pt/SrTiO_3$ photocatalysts containing 0.5 wt % (0.5 wt % Pt), 1.0 wt % (1.0 wt % Pt), 1.5 wt % (1.5 wt % Pt), and 2.0 wt % (2.0 wt % Pt) of platinum relative to a total weight of each $Pt/SrTiO_3$ photocatalyst for photocatalytic oxidation of cyclohexane.

FIG. 7 shows the effect of the doped Pt weight percentage on the photocatalytic activities of $SrTiO_3$ nanoparticles and $Pt/SrTiO_3$ photocatalysts for photocatalytic oxidation of cyclohexane. The results show that the photocatalytic activity was significantly enhanced, as demonstrated by increasing conversion of cyclohexane of 5.0%, 75%, 85%, and 100% by using $SrTiO_3$, 0.5 wt % $Pt/SrTiO_3$, 1.0 wt % $Pt/SrTiO_3$, 1.5 wt % $Pt/SrTiO_3$, and 2.0 wt % $Pt/SrTiO_3$, respectively. Such enhancement in catalytic activity due to the doping $SrTiO_3$ nanoparticles with noble metals such as Pt [Neppolian B, Mine S, Horiuchi Y, Bianchi C L, Matsuoka M, Dionysiou D D and Anpo M 2016. Efficient photocatalytic degradation of organics present in gas and liquid phases using $Pt$—$TiO_3$/Zeolite (H-ZSM) Chemosphere 153, 237, incorporated herein by reference in its entirety]. Moreover, the photocatalytic activity did not change after weight percentage of doped metallic Pt reached 1.5 wt %. Therefore, the weight percentage of doped metallic Pt affected the electron-hole recombination rate and band gap of $SrTiO_3$ nanoparticles. Nevertheless, it can be concluded that 1.5 wt % $Pt/SrTiO_3$ photocatalyst exhibited the uppermost photocatalytic activity, lowest electron-hole recombination rate and band gap.

The stability of the $Pt/SrTiO_3$ nanoparticles for the photocatalytic oxidation of cyclohexane was investigated using the 1.5 wt % $Pt/SrTiO_3$ photocatalyst. It was verified that the 1.5 wt % $Pt/SrTiO_3$ photocatalyst maintained high photocatalytic stability after being used five successive times [Pol R, Guerrero M, Garcia-Lecina E, Altube A, Rossinyol E, Garroni S, Baró M D, Pons J. Sort J and Pellicer E 2016, Ni-, Pt- and (Ni/Pt-doped $TiO_2$ nanophotocatalysts: A smart approach for sustainable degradation of Rhodamine B dye Appl Catal, B 181, 270, incorporated herein by reference in its entirety].

The invention claimed is:

1. A process of oxidizing a cycloalkane to a cycloalkanol and/or a cycloalkanone, the process comprising:
    contacting a feed mixture comprising the cycloalkane and an oxidant with a $Pt/SrTiO_3$ photocatalyst thereby forming a reaction mixture; and
    concurrently irradiating the reaction mixture with light thereby forming the cycloalkanol and/or the cycloalkanone;
    wherein the $Pt/SrTiO_3$ photocatalyst comprises:
        strontium titanate nanoparticles; and
        platinum doped on a surface of the strontium inmate nanoparticles;
        wherein the platinum is present in an amount of 0.1-5.0 wt % relative to a total weight of the $Pt/SrTiO_3$ photocatalyst.

2. The process of claim 1, wherein the $Pt/SrTiO_3$ photocatalyst has a crystallite size of 8-30 nm.

3. The process of claim 1, wherein the Pt/SrTiO$_3$ photocatalyst has a BET surface area of 5-25 m$^2$/g.

4. The process of claim 1, wherein the Pt/SrTiO$_3$ photocatalyst has an absorption peak in a range of 360-380 nm, and a band gap energy of 2.5-3.6 eV.

5. The process of claim 1, wherein the Pt/SrTiO$_3$ photocatalyst has a photoluminescence peak in a range of 380-480 nm upon excitation at a wavelength of 270-290 nm.

6. The process of claim 1, wherein the light has a wavelength of 400-800 nm.

7. The process of claim 1, wherein the feed mixture is contacted with the Pt/SrTiO$_3$ photocatalyst at a pressure of 0.5-2 atm.

8. The process of claim 1, wherein the feed mixture is contacted with the Pt/SrTiO$_3$ photocatalyst at a temperature of 40-80° C.

9. The process of claim 1, wherein the cycloalkane is present in the feed mixture at a concentration of 10-400 ppm.

10. The process of claim 1, wherein the oxidant is present in an amount of 5-30 vol. % relative to a total volume of the feed mixture.

11. The process of claim 1, wherein the Pt/SrTiO$_3$ photocatalyst is present at a concentration of 0.2-5.0 g of photocatalyst per liter of the reaction mixture.

12. The process of claim 1, wherein the oxidant is O$_2$.

13. The process of claim 1, wherein the feed mixture further comprises an inert gas.

14. The process of claim 1, wherein the feed mixture further comprises water.

15. The process of claim 1, which has a molar conversion of the cycloalkane to the cycloalkanol and/or the cycloalkanone of greater than 40%.

16. The process of claim 1, wherein the cycloalkane is cyclohexane, the cycloalkanol is cyclohexanol, and the cycloalkanone is cyclohexanone.

17. The process of claim 1,
wherein the platinum is present in an amount of 1.3-3.0 wt % relative to a total weight of the Pt/SrTiO$_3$ photocatalyst;
wherein the reaction mixture is irradiated with light for 1 to 4 hours; and
wherein the process has a molar conversion of the cycloalkane to the cycloalkanol and/or cycloalkanone of greater than 95%.

18. The process of claim 1, further comprising:
recovering the Pt/SrTiO$_3$ photocatalyst after the irradiating to obtain a recovered Pt/SrTiO$_3$ photocatalyst; and
reusing the recovered Pt/SrTiO$_3$ photocatalyst, which maintains photocatalytic activity for at least 4 reaction cycles.

* * * * *